United States Patent [19]

Ullrich

[11] Patent Number: 5,696,081
[45] Date of Patent: Dec. 9, 1997

[54] UVB-INDUCED FACTOR FOR IMMUNOSUPRESSION

[75] Inventor: Stephen E. Ullrich, Houston, Tex.

[73] Assignee: Board of Regents, The University Of Texas System, Austin, Tex.

[21] Appl. No.: 427,629

[22] Filed: Apr. 24, 1995

Related U.S. Application Data

[60] Continuation of Ser. No. 127,272, Sep. 24, 1993, abandoned, which is a division of Ser. No. 768,232, filed as PCT/US90/01402 Mar. 14, 1990, abandoned, which is a continuation-in-part of Ser. No. 323,615, Mar. 14, 1989, abandoned.

[51] Int. Cl.$^6$ .......................... A61K 41/00; A61K 38/02
[52] U.S. Cl. .................. 514/8; 514/21; 514/885; 424/278.1; 530/868
[58] Field of Search .................. 514/8, 885, 21; 424/184.1, 278.1; 530/868

[56] References Cited

U.S. PATENT DOCUMENTS

| | | | |
|---|---|---|---|
| 4,977,244 | 12/1990 | Muchmore et al. | 530/350 |
| 5,095,095 | 3/1992 | Fontana | 530/350 |
| 5,109,116 | 4/1992 | Arkwright et al. | 530/395 |

FOREIGN PATENT DOCUMENTS 8705911  10/1987  WIPO.

OTHER PUBLICATIONS

Kripke, "Immunological Unresponsiveness Induced by Ultraviolet Radiation", *Immunol. Rev.*, No. 80 (1984) 87–102.

Kripke et al., In vivo Immune Responses of Mice During Carcinogenesis by Ultraviolet Irradiation, *J. Natl. Can. Inst.*, vol. 59 (1977) 1227–1230.

Noonan et al., Suppression of Contact Hypersensitivity by Ultraviolet Radiation: An Experimental Model, *Springer Semin. Immunopath.*, vol. 4 (1981) 293–304.

Greene et al., Impairment of Antigen–Presenting Cell Function by Ultraviolet Radiation, *Proc. Natl. Acad. Sci. U.S.A.*, vol. 76 (1979) 6591–6595.

Ullrich et al., Suppression of the Induction of Delayed–Type Hypersensitivity Reactions in Mice by a Single Exposure to Ultraviolet Radiation, *Photochem. Photobiol.*, vol. 43 (1986) 633–638.

Ullrich, Suppression of the Immune Response to Allogeneic Histocompatibility Antigens by a Single Exposure to Ultraviolet Radiation, *Transplantation*, vol. 42 (1986) 287–291.

Molendijk et al., Suppression of Delayed–Type Hypersensitivity to Histocompatibility Antigens by Ultraviolet Radiation, *Immunology*, vol. 62 (1987) 299–305.

Swartz, Role of UVB–Induced Serum Factor(s) in Suppression of Contact Hypersensitivity in Mice, *J. Invest. Dermatol.*, vol. 83 (1984) 305–307.

Harriott–Smith et al., Circulating Suppressor Factors in Mice Subjected to Ultraviolet Irradiation and Contact Sensitization, *Immunology*, vol. 57 (1986) 207–211.

DeFabo et al., Mechanism of Immune Suppression by Ultraviolet Irradiation in vivo, I. Evidence for the Existence of Unique Photoreceptor in Skin and its Role in Photoimmunology, *J. Exp. Med.*, vol. 158 (1983) 84–98.

Ross et al., Ultraviolet–Irradiated Urocanic Acid Suppresses Delayed–Type Hypersensitivity to Herpes Simplex Virus in Mice, *J. Invest. Dermatol.*, vol. 87 (1986) 630–633.

Noonan et al., Cis–Urocanic Acid, a Product Formed by Ultraviolet B Irradiation of the Skin, Initiates an Antigen Presentation Defect in Splenic Dendritic Cells in vivo, *J. Invest. Dermatol.*, vol. 90 (1988) 92–99.

Robertson et al., In vivo Administration of Interleukin 1 to Normal Mice Depresses their Capacity to Elicit Contact Hypersensitivity Responses: Prostaglandins Are Involved in this Modification of Immune Function, *J. Invest. Dermatol.*, vol. 88 (1987) 380–387.

Gahring et al., Effect of Ultraviolet Radiation on the Production of Epidermal Cell Thymocyte–Activating Factor/Interleukin 1 in vivo and in vitro, *Proc. Natl. Acad. Sci. USA*, vol. 81 (1984) 1198–1202.

Schwarz et al., Inhibition of the Induction of Contact Hypersensitivity by a UV–Mediated Epidermal Cytokine, *J. Invest. Dermatol.*, vol. 87 (1986) 289–291.

Fisher et al., Suppressor T Lymphocytes Control the Development of Primary Skin Cancers in Ultraviolet–Irradiated Mice, *Science*, vol. 216 (1982) 1133–1134.

Lau et al., Pancreatic Islet Allograft Prolongation by Donor–Specific Blood Transfusions Treated with Ultraviolet Irradiation, *Science*, vol. 221 (1983) 754–756.

Lau et al., Prolongation Rat Islet Allograft Survival by Direct Ultraviolet Irradiation of the Graft, *Science*, vol. 223 (1984) 607–609.

Yuspa et al., A Survey of Transformation Markers in Differentiating Epidermal Cell Lines in Culture, *Cancer Research*, vol. 40 (1980) 4694–4703.

(List continued on next page.)

*Primary Examiner*—James C. Housel
*Assistant Examiner*—Julie Krsek-Staples
*Attorney, Agent, or Firm*—Arnold White & Durkee

[57] ABSTRACT

The present invention comprises the method of selectively suppressing an immune response of a mammal to a particular alloantigen. The method includes several steps. One step is administering to a mammal an effective amount of UVB-radiation. Epidermal cell cultures, when subjected to UVA or UVB irradiation produce specific immunosuppressive factors. This UV-radiation is preferably UVA radiation (320 nm to 400 nm), or UVB-radiation (280 nm to 320 nm). It is demonstrated herein that UVA radiation results in in vitro cells producing a factor which selectively suppresses the CHS response in mammals, while UVB radiation selectively suppresses the DTH response in mammals. Another step of the inventive method involves desensitizing a mammal to a particular alloantigen. It has been determined that a mammal will become tolerant to a particular alloantigen once the subject mammal has been irradiated with a pre-determined wavelength of UVR and thereafter sensitized with the particular alloantigen. This may analogously be accomplished using factors from in vitro epidermal cell cultures.

2 Claims, 13 Drawing Sheets

OTHER PUBLICATIONS

Shearer, Cell–Mediated Cytotoxicity to Trinitrophenyl–Modified Syngeneic Lymphocytes, Eur. J. Immunol., vol. 4 (1974) 527–533.

Mishell et al., Immunization of Dissociated Spleen Cell Cultures from Normal Mice, J. Exp. Med., vol. 126 (1967) 423–442.

Jerne et al., Plaque Formation in Agar by Single Antibody Producing Cells, Science, vol. 140 (1963) 405.

Dunnett, A Multiple Comparison Procedure for Comparing Several Treatments with a Control, J. Am. Stat. Assoc., vol. 50 (1955) 1096–1121.

Storb, Critical Issues in Bone Marrow Transplantation, Transplantation Proc., vol. 19 (1987) 2774–2781.

Klein et al., Participation of H–2 Regions in Heart–Transplant Rejection, Transplantation, vol. 22 (1976) 384–390.

Korngold et al., Surface Markers of T Cells Causing Lethal Graft vs. Host Disease to Class I vs. Class II H–2 Differences, J. Immunol., vol. 135 (1985) 3004–3010.

Fidler, The Relationship of Embolic Homogeneity, Number, Size and Viability to the Incidence of Experimental Metastases, Eur. J. Cancer, vol. 9 (1973) 223–227.

Kripke, Latency, Histology, and Antigenicity of Tumors Induced by Ultraviolet Light in Three Inbred Mouse Strains, Can. Res., vol. 37 (1977) 1395–1400.

Ullrich et al., Mechanisms in the Suppression of Tumor Rejection Produced in Mice by Repeated UV Irradiation, J. Immunol., vol;. 133 (1984) 2786–2790.

Ullrich et al., Suppressor Lymphocytes Induced by Epicutaneous Sensitization of UV–Irradiated Mice Control Multiple Immunological Pathways, Immunology, vol. 58 (1986) 185–190.

Ullrich et al., Specific Suppression of Allograft Rejection after Treatment of Recipient Mice with Ultraviolet Radiation and Allogeneic Spleen Cells, Transplantation, vol. 46 (1988) 115–119.

Everett et al., Penetration of Epidermis by Ultraviolet Rays, Photochem. Photobiol., vol. 5 (1966) 533–542.

Ross et al., Systemic Administration of Urocanic Acid Generates Suppression of the Delayed Type Hypersensitivity Response to Herpes Simplex Virus in a Murine Model of Infection, Photodermatology, vol. 5 (1988) 9–14.

Schwarz et al., Uv–Irradiated Epidermal Cells Produce a Specific Inhibitor of Interleukin 1 Activity, J. Immunol., vol. 138 (1987) 1457–1463.

Liew et al., Regulation of Delayed–Type Hypersensitivity. Vi. Antigen–Specific Suppressor T Cells and Suppressor Factor for Delayed–Type Hypersensitivity to Histocompatibility Antigens, Transplantation, vol. 33 (1982) 69–76.

Swartz, Suppression of Delayed–Type Hypersensitivity to Radiation [UV, 280-320 mm (UVB)]–Induced Tumor Cells with Serum Factors from UVB–Irradiated Mice, J. Natl. Can. Inst., vol. 76 (1986) 1181–1184.

Kupper et al., Interleukin 1 Gene Expression in Cultured Human Keratinocytes Is Augmented by Ultraviolet Irradiation, J. Clin. Invest., vol. 80 (1987) 430–436.

Ansel et al., The Expression and Modulation of IL–1 Alpha in Murine Keratinocytes, J. Immunol., vol. 140 (1988) 2274–2278.

Kripke, et al., Studies on the mechanism of systemic suppression of contact hypersensitivity by UVB radiation. II. Differences in the suppression of delayed and contact hypersensitivity in mice, J. Invest. Dermatol., vol. 74 (1986) 543–549.

Gensler et al., Item 1 from file 265, Dialog (abstract only).

Berger et al., Item 3 from file 265, Dialog (abstract only).

Noonan, Item 5 from file 265, Dialog (abstract only).

Noonan, Item 6 from file 265, Dialog (abstract only).

Elmets, Item 24 from file 265, Dialog (abstract only).

Pierpaoli et al., European Patent Application Item 5 from file 351, Dialog (abstract only).

Oluwole et al., Item 27/5/1 Embase (abstract only).

Granstein et al., Item 27/5/6 Embase (abstract only).

Morison et al., Item 27/5/13, Embase (abstract only).

Morison et al., Item 34/5/10, Embase (abstract only).

Kupper et al., Immunoregulation after Thermal Injury: Sequential Apperance of I–J$^+$, Ly–1 T Suppressor Inducer Cells and Ly–2 T Suppressor Effector Cells Following Thermal Trauma in Mice, J. Immunol., vol. 135 (1984) 3047–3053.

International Search Report for corresponding International Patent Application No. PCT/US 90/01402, Jul. 19, 1990.

Kim. Tae-Yoon et al., Immunosuppression by factors released from UV–irradiated epidermal cells: Selective effects on the generation of contact and delayed hypersensitivity after exposure to UV–a or UV–B radiation, Biological Abstracts, vol. 89 (1990) and J. Invest. Dermatol. 94(1):26–32 (1990) (abstract 48803).

Ullrich et al., Induction of suppressor cells by a factor released by UV–irradiated epidermal cells, The Faseb Journal, vol. 2(6), 25 Mar. 1988 (p. A1680, abstract 8036).

Laemmli, U.K., Cleavage of structural proteins during the assembly of the head of the bacteriophage T4, Nature, 227:680 (1970).

Kripke, Margaret L. and McClendon, Evelyn, Studies on the Role of Antigen–Presenting Cells in the Systematic Suppression of Contact Hypersensitivity by UVB Radiation, The Journal of Immunology, 137(2):443–447 (1986).

Magee et al., Suppression of the Elicitation of the Immune Response to Alloantigen by Ultraviolet Radiation, Transplantation, 47(6):1008–1013 (1989).

Mottram et al., A single dose of UV radiation suppresses delayed type hypersensitivity responses to alloantigens and prolongs heart allograft survival in mice, Innunol. Cell Biol., 66(5–6):377–385 (1988) (Abstract only considered).

Tae-Yoon Kim et al, Clin Res 36(3):622A, 1988.

Bennett et al, Proc Natl Acad Sci USA, 77(10):6109–6113, 1980.

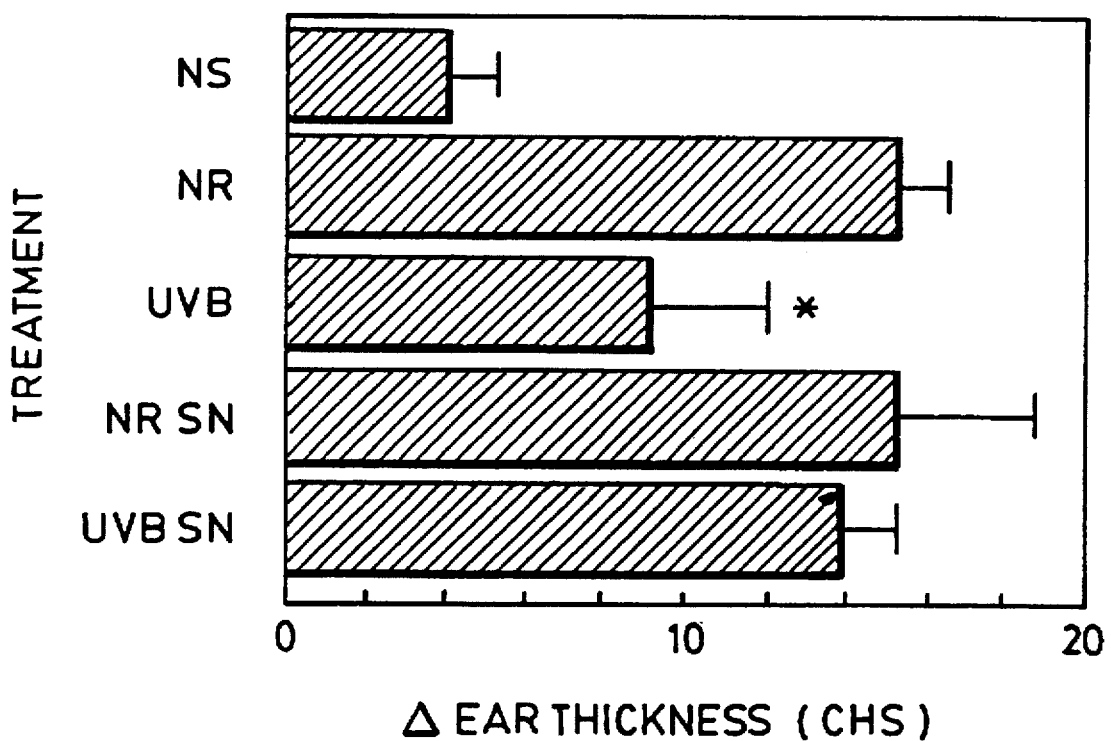

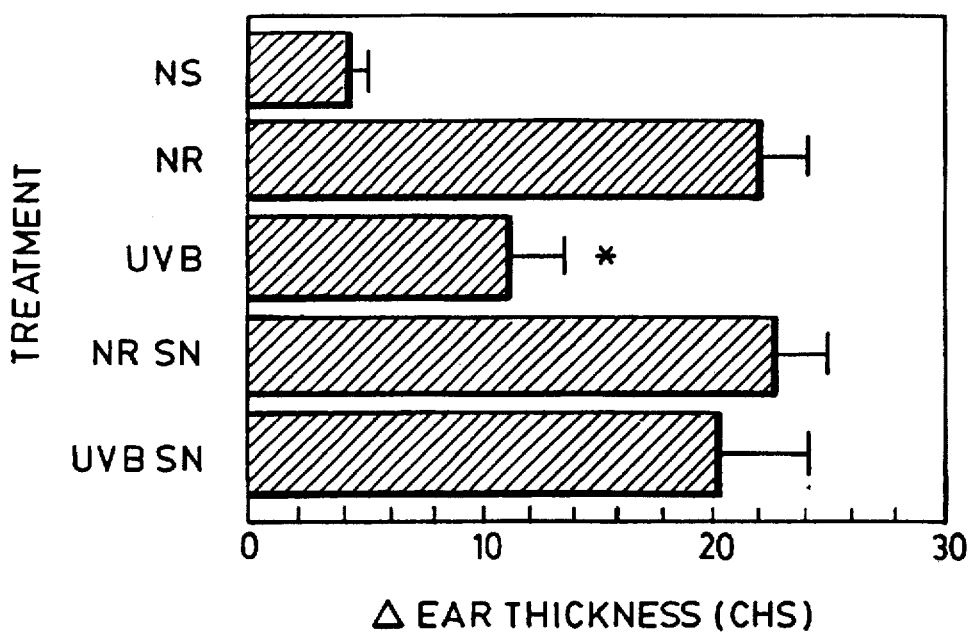

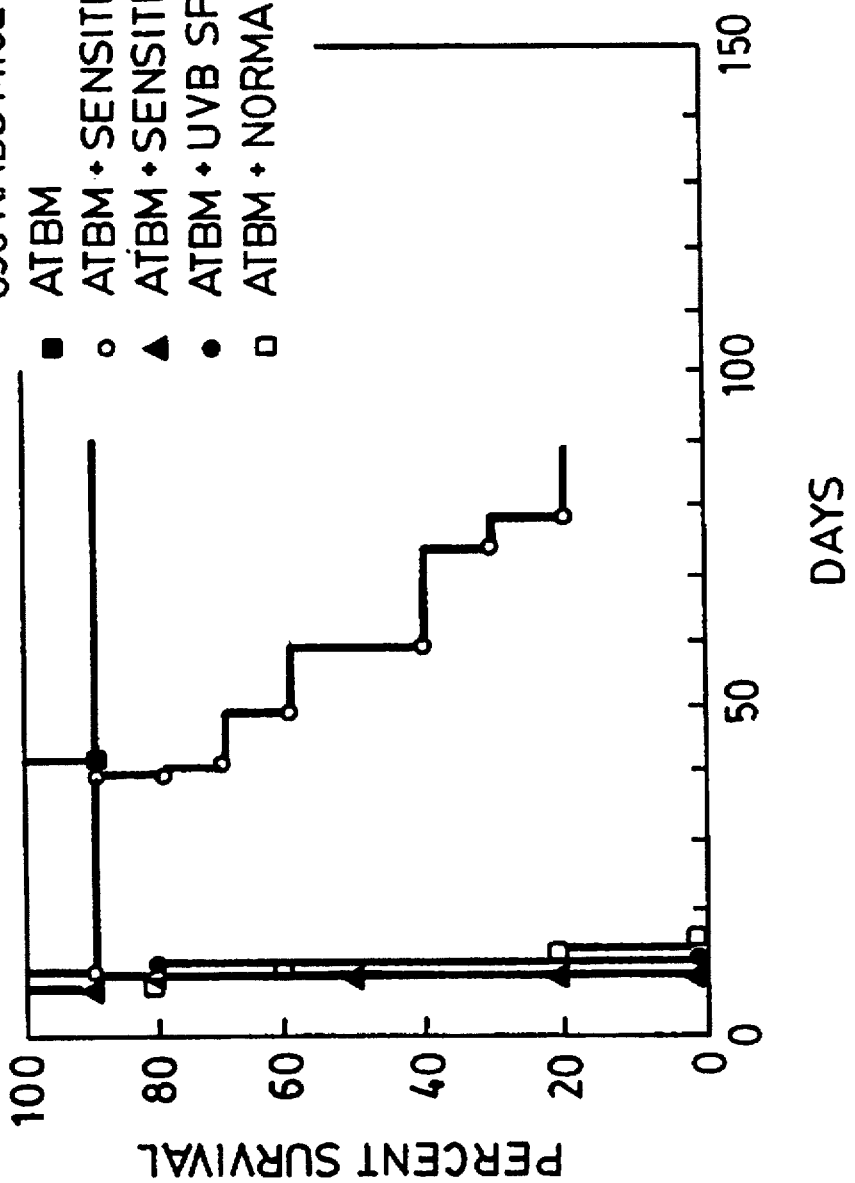

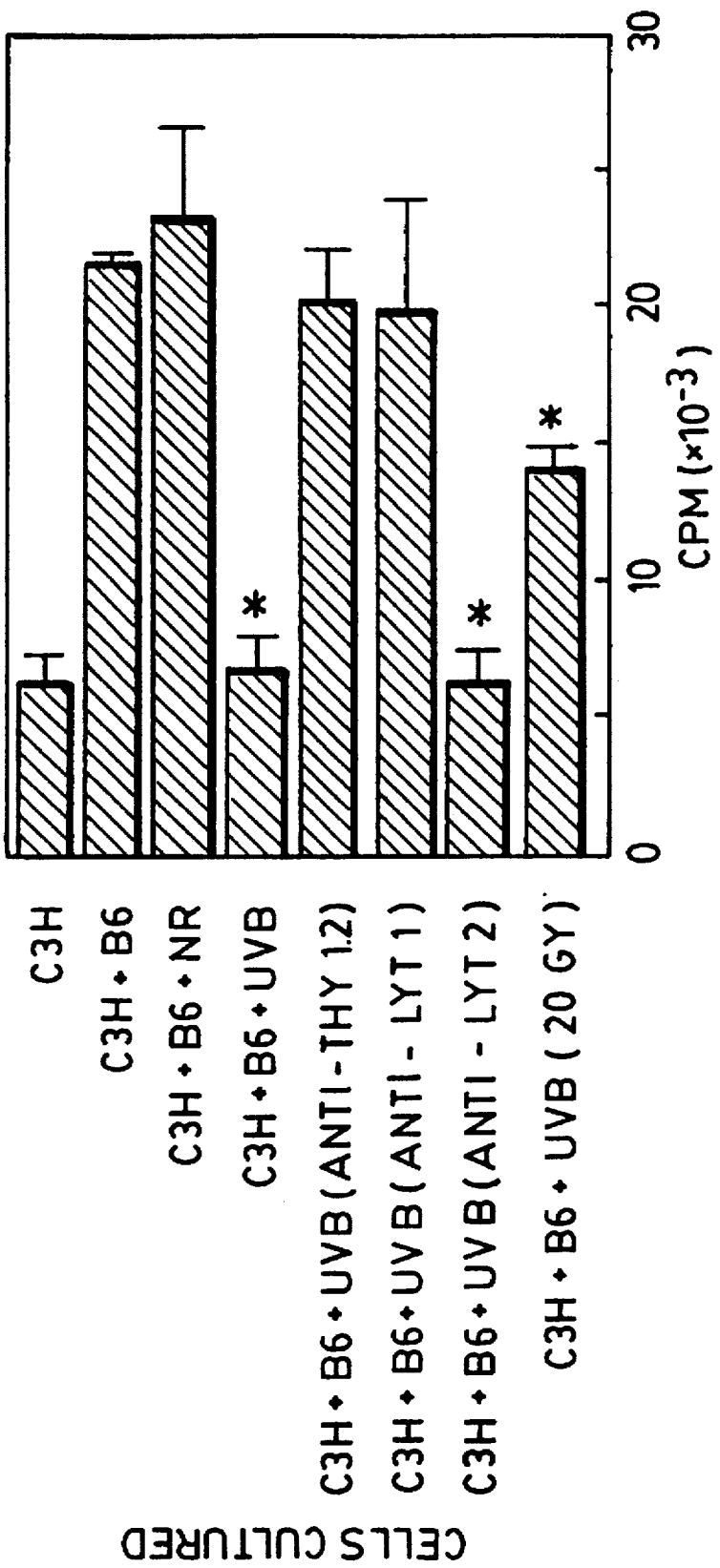

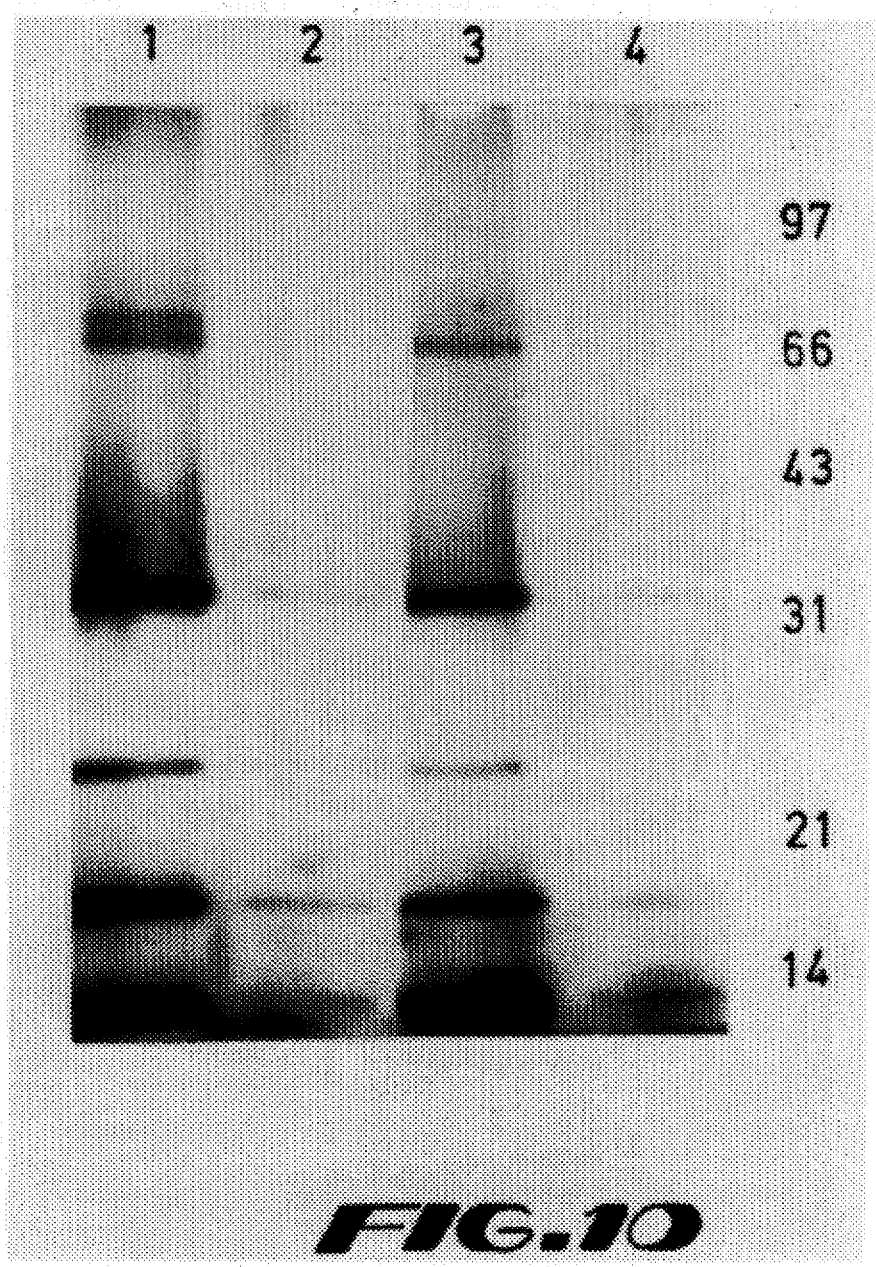

UVB-INDUCED FACTOR FOR IMMUNOSUPRESSION

This application is a continuation of application Ser. No. 08/127,272 filed Sep. 24, 1993, now abandoned, which is a divisional of application Ser. No. 07/768,232 filed Oct. 10, 1991, now abandoned, which is the national stage filed Mar. 14, 1990 under 35 USC 371 of PCT/US90/01402, which is a continuation-in part of Ser. No. 07/323,615 filed Mar. 14, 1989, now abandoned.

In addition to its carcinogenic effect, ultraviolet (UV) radiation suppresses the immune response [1]. The diminished capacity of mice exposed to subcarcinogenic doses of UV radiation to reject highly antigenic UV-induced tumors has been attributed to a suppression of the immune response of UV-irradiated recipient mice [2]. Mice exposed to a single dose of UV radiation are unable to generate a contact hypersensitivity (CHS) reaction to contact allergens applied to a distant unirradiated site [3]. In a similar manner, a single exposure to UV radiation also inhibits the generation of a delayed hypersensitivity (DTH) response to hapten modified cells [4], foreign erythrocytes and protein antigens [5] and allogeneic spleen cells [6,7].

The mechanism by which UV-radiation induces a systemic suppression of the immune response is not entirely clear. Recent studies have suggested that the release of soluble factors from UV-irradiated epidermal cells contribute to the induction of suppression. Swartz [8] found that when serum from UV-irradiated animals was transferred into normal recipients, their ability to respond to contact allergens was significantly suppressed. Harriott-Smith and Halliday [9] also described the presence of suppressive factors in the serum of UV-irradiated mice. DeFabo and Noonan [10] have suggested that the photoreceptor for UV-radiation in the skin may be urocanic acid. They suggest that the photoisomerization of trans-urocanic acid to cis-urocanic acid by UV-radiation is essential in the induction of systemic suppression. Data to support this hypothesis comes from the experiments of Ross et al. [11] and Noonan etal. [12] that demonstrate that the injection of cis-urocanic acid can suppress the DTH response to Herpes Simplex Virus and result in the impairment of splenic antigen-presenting cell function.

An alternative hypothesis comes from the studies of Robertson et al. [13]. The injection of recombinant interleukin-1 (IL-1) into mice prevented them responding to contact allergens. Suppressor cells were found in the spleens of these mice that could inhibit the elicitation of CHS When transferred into sensitized animals. The suppression appears to be dependent on the release of prostaglandin since the administration of the prostaglandin synthetase inhibitor indomethacin abrogated the suppressive effect. These authors suggest that the inflammation caused by UV-radiation exposure results in the release of substances such as IL-1 and prostaglandins which play a role in the induction of the systemic suppression. Studies by Gabring et al. [14] demonstrating an increased level of IL-1 in the serum of UV-irradiated mice support this hypothesis. It should be noted, however, that Harriott-Smith and Halliday in their study [9] were unable to document the presence of IL-1 in the serum samples that suppressed CHS. Finally, Schwarz et al. [15] showed that IV-exposure of primary epidermal cell cultures and/or a keratinocyte cell line in vitro resulted in the release of soluble factors into the supernatant. Injection of the supernatant into mice mimicked the effect of whole body UV-irradiation and suppressed the animals ability to respond to contact allergens. Notably, Schwarz et al. [8] determined that indomethacin did not abrogate the production of the suppressive factor.

The study of the systemic suppression of the immune system by UV-radiation is important for a number of reasons. First, an association between immunosuppression and the development of primary skin cancers in mice has been demonstrated [16]. Insight into the mechanism by which UV-radiation suppresses the immune response may be helpful in providing new approaches for the treatment and/or prevention of skin cancer. Second, the systemic immunologic alterations caused by UV-radiation, especially the suppression of DTH, may be a predisposing factor for an increased incidence of infectious diseases. This coupled with a decrease in the atmospheric ozone layer suggests that UV-induced immunosuppression may adversely affect the health of wide segments of the population. Finally, the immunosuppression induced by UV-radiation may have therapeutic applications, e.g., in the suppression of allograft rejection.

Although it is yet to be determined what the mechanism of UV-induced CHS and DTH suppression is, it has generally been considered by researchers in this area that a single mechanism is responsible for both. However, the present inventor has demonstrated that at least two factors are involved, each being released by cells after irradiation with different wavelengths of UV-radiation. The present inventor has determined that supernatant from epidermal cells exposed to long-wave UV radiation, UVA, (320–400 nm) would suppress CHS but not DTH. On the other hand, supernatants from short-wave UV-radiation, UVB, (280–320 nm) would suppress DTH but not CHS. This result shows that two different immunosuppressive factors are released by UV-irradiated cells. The first immunosuppressive is released on exposure to UVB and suppresses DTH and the second is released on exposure to UVA and suppresses CHS. Therefore, by using a pre-determined wavelength of ultraviolet radiation (UVR), e.g., UVA or UVB, the immune response of a mammal can be selectively suppressed.

Typically, to overcome the immunological rejection of transplanted tissue (allografts), immunosuppressive drugs are used. One serious side effect of many of these agents, however, is the pan-immunosuppression that is produced. In addition to the suppression of allograft rejection, all other immune responses, such as those involved in the protection of the host from viral and bacterial pathogens, are also suppressed. As a result the immunosuppressed patient is susceptible to a variety of opportunistic infections. Accordingly, a method of suppressing only the immune response to the allografted tissue while leaving other immunological functions intact would be highly advantageous.

It has been reported that direct UV-irradiation (UVR) of the allograft can result in prolonged survival (17, 18) of the allograft. The mechanism suggested there is an alteration of the antigenic composition of the grafted tissue by the UVR, thus rendering the allograft nonantigenic. In the present invention, however, an alternative approach of rendering the recipient tolerant to the allograft is taken.

In the present invention specific immunosuppressive factors are produced in vivo, by a subject mammal, or in vitro, by a mammalian cell, when either is irradiated with a sufficient amount of a pre-determined wavelength of UVR. These immunosuppressive factors, combined with subsequent antigenic sensitization of an animal, induce an immunosuppression which is specific for the antigenic determinants used to sensitize the animal. Thus, pan-immunosuppression is avoided. In this regard the use of a pre-determined wavelength of UVR to induce selective immunosuppression may have a marked advantage over the use of immunosuppressive drugs such as azathioprine or corticosteriods. Accordingly, the method of administering a sufficient amount of a pre-determined wavelength of UVR to selectively suppress an immune response in a mammal to a particular alloantigen would have advantageous applications in the suppression of allograft rejection after organ transplantation. For example, it would be advantageous to use the methods of the present invention to selectively suppress DTH and allograft rejection while leaving the immune system of a patient otherwise uncompromised.

One aspect of the present invention comprises the method of selectively suppressing an immune response of a mammal to a particular alloantigen. The method includes several steps. One step is administering to a mammal an effective amount of UV-radiation having a pre-determined wavelength. The pre-determined wavelength of the UV-radiation is preferably UVB-radiation (280 nm to 320 nm). It is demonstrated herein that UVB radiation suppresses the CHS response and the DTH response in mammals. Another step of the inventive method involves desensitizing a mammal to a particular alloantigen. It has been determined that a mammal will become tolerant to a particular alloantigen once the subject mammal has been irradiated with a pre-determined wavelength of UVR and thereafter sensitized with the particular alloantigen.

Another aspect of the present invention is a method for selectively suppressing an immune response in a mammal to a particular alloantigen following the administration of immunosuppressive factors and subsequent sensitization of the mammal to the particular alloantigen. The method may include multiple steps. One step is irradiating a plurality of mammalian cells with a sufficient amount of UV-radiation having a pre-determined wavelength to create immunosuppressive factors. It has been determined that mammalian epidermal cells irradiated with UVB radiation (pre-determined wavelength of UVB-radiation being 280 to 320 nm) will produce immunosuppressive factors which selectively suppress the DTH response in mammals. On the other hand, it has been determined that mammalian epidermal cells irradiated with UVA-radiation (pre-determined wavelength of UVA-radiation being 320 nm to 400 nm) will produce immunosuppressive factors which selectively suppress the CHS response in mammals.

Another step in the inventive method involves extracting the immunosuppressive factors from the UV-irradiated cells. A further step in the inventive method involves administering an effective amount of the immunosuppressive factors to the mammal. Thereafter, the mammal is sensitized to the particular alloantigen for which immunotolerance is preferred.

Yet another aspect of the present invention is the process for producing immunosuppressive factors and the immunological suppressive factors themselves. This aspect of the invention preferably produces immunosuppressive factors which may be subsequently administered to a subject animal to result in a selective suppression of a specific immune response to a particular alloantigen. The inventive process includes the steps of radiating a plurality of mammalian cells in vitro with a sufficient amount of a pre-determined wavelength of UV-radiation to produce UV-irradiated cells producing immunosuppressive factors. It has been determined that mammalian cells irradiated in vitro with a sufficient amount of UVB (pre-determined wavelength being 280 to 320 nm) will produce immunosuppressive factors which selectively suppress the DTH response in mammals when administered in a sufficient amount. On the other hand, it has also been determined that mammalian cells irradiated with UVA (pre-determined wavelength being 320 nm to 400 nm) will produce immunosuppressive factors which selectively inhibit the CHS response in mammals when administered in a sufficient amount.

A single exposure to ultraviolet radiation induces a systemic suppression of the immune response to allogeneic histocompatibility antigens. The suppression is associated with the appearance of splenic alloantigen-specific suppressor T cells. How exposing the skin to UV radiation results in the induction of splenic suppressor T cells is not entirely clear. The data described herein suggest the involvement of a UV-induced keratinocyte-derived suppressive factor. The keratinocyte line, Pam 212 was exposed to 200 J/m$^2$ of UVB radiation from a single FS-40 sunlamp and cultured overnight in serum-free medium. Injecting mice with culture supernatants from UV-irradiated keratinocytes suppressed the induction of delayed type hypersensitivity to alloantigen. Injecting supernatants from non-irradiated Pam 212 cells had no suppressive effect. Antigen-specific T suppressor cells were found in the spleens of the mice injected with the suppressive supernatants. Cycloheximide treatment of keratinocytes and trypsinization of the supernatants from the UV-irradiated keratinocytes resulted in a loss of suppressive activity suggesting the involvement of a protein. The suppressive material bound to a Concanavalin A-agarose lectin-affinity column and was eluted with α-D-mannopyranoside, indicating that the suppressive material is a glycoprotein. Analysis of the suppressive material and the control supernatants by polyacrylamide gel electrophoresis demonstrated a prominent band in the suppressive fractions that was not present in the non-suppressive fractions. The approximate molecular weight of the unique band was 68 kilodaltons. Thus, these data support the hypothesis that soluble factors released from UV-irradiated keratinocytes are responsible for the induction of systemic suppression following exposure to UV radiation, by demonstrating that the injection of these factors induces antigen-specific suppressor T cells.

BRIEF DESCRIPTION OF THE DRAWINGS

FIG. 1A and 1B show the effect of the supernatants from UV-irradiated primary epidermal cell cultures on the induction of CHS(A) or DTH(B). Mice were injected with supernatants from the UVB-irradiated (UVB-SN) or control (NRSN) epidermal cell cultures or exposed to 40 kJ/m$^2$ of UVB radiation (UVB). In FIG. 1A, C3H mice were sensitized with TNCB, in FIG. 1B, C3H mice were sensitized with BALB/c spleen cells. The asterisk indicates a significant difference (P<0.001) from the response observed in the positive control (NR). The background response was measured in mice that were challenged but not sensitized with the antigen (NS). There were 5 mice per group: units=cm×10$^{-3}$.

FIG. 2A and 2B show the effect of the supernatants from UV-irradiated Pam 212 cells on the induction of CHS(A) or DTH(B). Mice were injected with supernatants from the UV-irradiated (UVSN) or control (NRSN) non-irradiated keratinocyte cell cultures or exposed to 40 kJ/m$^2$ of UVB radiation (UVB). In FIG. 2A Balb/c mice were sensitized with TNCB, in FIG. 2B, Balb c mice were sensitized with C3H spleen cells. The asterisk indicates a significant difference (P<0.001) from the response observed in the positive control (NR). The background response was measured in mice that were challenged but not sensitized with the antigen (NS). There were 5 mice per group; units=cm×10$^{-3}$.

FIG. 5 shows the effect of UVB radiation and antigenic sensitization on GVHD. Lethally X-irradiated (850 rads) BALB/c mice were reconstituted with 5×10$^6$ T cell-depleted C3H bone marrow cells (ATMB), anti-Thy 1.2 monoclonal antibody, Becton Dickinson, Mountain View, Calif.: plus complement) and 5×10$^5$ C3H spleen cells. ATMB only (solid squares). Spleen cells were obtained from normal control mice (open squares); mice exposed to UVB only (solid circles); mice sensitized with alloantigen (solid triangles); or mice expose to .UVB and sensitized with alloantigen (open circles). The animals were checked daily for morbidity and mortality. The experiments was terminated at 90 days. Statistical differences between the median survival times was determined by use of the Wilcoxon rank-sum test, P<0.001: ATBM+sensitized UVB spleen cells vs. ATBM +sensitized NR spleen cells, n=10.

FIG. 6 shows the phenotype of the suppressor cells induced by injecting supernatants from UV-irradiated keratinocytes into mice. Spleen cells from mice injected with supernatants from the UV-irradiated keratinocytes where added to one way MLR cultures containing normal C3H responder cells and gamma-irradiated B6 stimulator cells. Spleen cells from the mice injected with the suppressive cytokines were treated with various monoclonal antibodies and complement. One group of cells was exposed to 72000. rad of gamma radiation. Control cells (UV and NR) were treated with complement. * indicates a significant difference from the proliferation of the control; P<0.001.

FIG. 7A and 7B show physical properties of the suppressive cytokine released from UV-irradiated keratinocytes. In FIG. 7A Pam 212 cells were exposed to 200 J/m$^2$ of UV radiation and then treated with 10 micrograms/ml of indomethacin or 10 microgram/ml of cycloheximide. Supernatants from the treated cells and the control cultures (UV and NR) were dialyzed and then injected into mice. In FIG. 7B the supernatants were harvested and then treated with heat or trypsin (10 microgram/ml). The treated-supernatants were then injected into mice and the resulting MLR was measured. The background response of responder cells cultured alone was 4290±960 CPM. * indicates a significant difference from the control; P<0.001.

FIG. 10 shows sodium dodecyl sulfate-polyacrylamide gel electrophoresis (SDS-PAGE) analysis of the suppressive material eluted from conconavalin-A (Con A)-agarose columns. Equivalent amounts (200 ng) of the material eluted from the Con A-agarose columns were analyzed on 12.5% SDS-PAGE gels under reducing conditions. Lane 1 contained the UV mannoside eluate, lane 2 the UV glucoside eluate, lane 3 the control mannoside eluate from non-irradiated cells, lane 4 the control glucoside eluate from non-irradiated cells. A unique band, present only in the immunosuppressive fraction (lane 1), and not in any of the non-suppressive fractions (lane 2-4), appears to migrate with a molecular weight of 68 kDa.

Figure 1B:
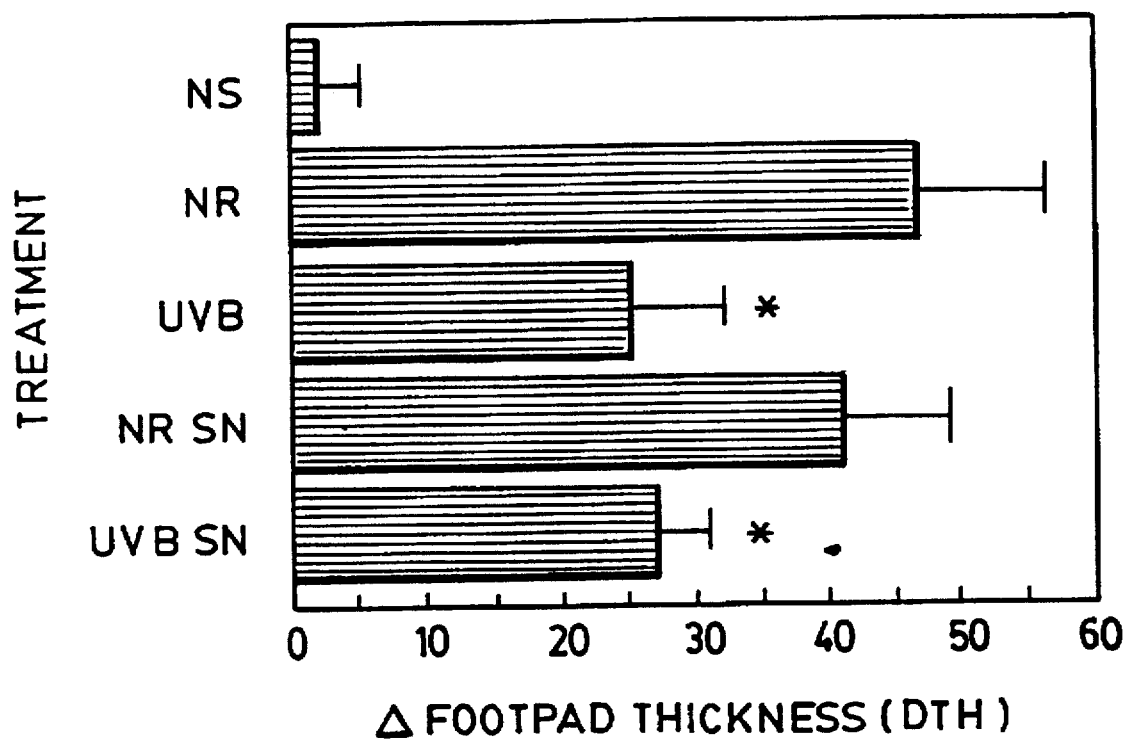

The selective suppression of a specific immune response to a particular alloantigen by a pre-determined wavelength of ultraviolet radiation is illustrated by experiments in which mice are irradiated with a sufficient dose of UV-radiation and subsequently sensitized to particular alloantigen. According to one preferred embodiment, the CHS response to the particular alloantigen is depressed by whole body UVB-irradiation (pre-determined wavelength 280 nm–320 nm) and subsequent sensitization with the particular alloantigen. Whole body irradiation is defined as the process of irradiating the epidermis of the subject animal. According to another preferred embodiment, the DTH response to a particular alloantigen is suppressed by whole body UVB-irradiation (pre-determined wavelength 280 nm–320 nm) and subsequent sensitization with the particular alloantigen.

The mechanism of whole body UV-induced immunosuppression is the release of immunosuppressive factors by UV-irradiated cells.

However, the present inventor has demonstrated that these immunosuppressive factors are contained in the supernatants from epidermal cell cultures exposed to pre-determined wavelengths of UV-radiation. Moreover, the immunosuppressive factors produced in vitro are potent, suppressing the induction of CHS or DTH, depending on the wavelength of UV-radiation used. In addition, it should be noted that the suppression induced by these immunosuppressive factors remains selective in nature. Thus, cells in vitro irradiated with selected or pre-determined wavelengths of UV-radiation, e.g., UVA (320 nm to 400 nm), or UVB (280 nm to 320 nm), produce immunosuppressive factors which, when administered to a subject individual, will selectively suppress an immune response in the subject individual. Accordingly, the immune response of the subject individual is not totally incapacitated, leaving much of the immune response uncompromised to protect against opportunist pathogens.

One aspect of the present invention is directed to the suppression of a specific immune response to a particular alloantigen in a mammal by administering immunosuppressive factors obtained from UV-irradiated cells to the subject mammal, thereafter sensitized to the particular alloantigen. Another aspect of the present invention is directed to the suppression of a specific immune response to a particular alloantigen by whole body UV-irradiation and subsequent sensitization to the particular alloantigen. The inventor has demonstrated that immunosuppressive factors released from either UVB-irradiated Pam 212 cells or primary epidermal cell cultures can mimic the effects of whole-body UVB-irradiation and suppress DTH. On the other hand, these same immunosuppressive factors were unable to suppress CHS. However, keratinocytes irradiated with UVA-radiation were able to generate a immunosuppressive factor that suppressed CHS. Moreover, the injection of the immunosuppressive factors from the UVA-irradiated keratinocytes did not suppress DTH. Thus, the present inventor has shown that the immunosuppressive factors released from UV-irradiated epidermal cells are responsible for the induction of selective systemic immunosuppression by UV-radiation. The data presented herein shows for the first time that the selective systemic immunosuppression by UV-radiation is controlled by two immunosuppressive factors, each one released after irradiation of cells with different wavelengths of UV radiation.

One aspect of the invention is directed to a method for selectively suppressing an immune response of a mammal to a particular alloantigen. This inventive method includes the steps of: (a) administering to a mammal an effective amount of UV-radiation having a pre-determined wavelength; and (b) sensitizing the animal thereafter to the particular alloantigen.

The first step in the inventive method is administering an effective amount of UV-radiation having a pre-determined wavelength to a mammal. In the most preferred embodiment, the UV-radiation is UVB-radiation having a pre-determined wavelength of 280 nm–320 nm. The UV-radiation is preferably administered to the mammal by irradiating the epidermis of the mammal, e.g., whole body irradiation. The effective amount of the UV-radiation is preferably from about 10 to about 100 kJ/m² and most preferably, from about 30 to about 60 kJ/m².

The next step of the inventive method is sensitizing the mammal thereafter to the particular alloantigen. The mammal is preferably sensitized by the injection of the particular alloantigen. The injection may be intravenous, intraperitoneal, intramuscular, subcutaneous or intrathecal. According to one embodiment of the invention, the mammal is sensitized by the intramuscular injection of the particular alloantigen. According to a preferred embodiment of the invention, the mammal is sensitized by the subcutaneous injection of the particular alloantigen. According to another preferred embodiment, the mammal is sensitized by the epicutaneous application of the alloantigen.

It is demonstrated herein that sensitized UV-irradiated animals develop a specific immunotolerance to the sensitizing alloantigen. For example, mice irradiated with UVB-radiation have suppressed DTH responses to the particular sensitizing alloantigen and a suppressed CHS response to the particular sensitizing alloantigen. Accordingly, the DTH or CHS response in a mammal may be selectively suppressed to a particular alloantigen depending on the wavelength of the UV radiation administered to the mammal.

Another aspect of the present invention is directed to methods of making and using immunosuppressive factors which induce a specific immunotolerance to a particular alloantigen in a subject mammal. The inventive method includes the steps of: (a) irradiating a plurality of mammalian cells in vitro, with an effective amount of UV-radiation having a pre-determined wavelength to create UV-irradiated cells producing immunosuppressive factors; (b) extracting the immunosuppressive factors from the UV-irradiated cells; (c) administering an effective amount of the immunosuppressive factors to a mammal; and (d) sensitizing the mammal thereafter to the particular alloantigen.

The first step of the inventive method is irradiating a plurality of mammalian cells in vitro with an effective amount UV-radiation having a pre-determined wavelength to create UV-irradiated cells producing immunosuppressive factors. Preferred cells include epidermal cells and may be those of the subject to be treated. Preferably, the UV-radiation is UVB-radiation.

It is demonstrated herein that mammalian cells irradiated in vitro with an effective amount of UVA-radiation produce immunosuppressive factors which, when administered in an effective amount to a subject mammal which is subsequently sensitized to a particular alloantigen, selectively suppress the CHS response in that mammal to that particular alloantigen. On the other hand, it has been demonstrated that mammalian cells irradiated in vitro with an effective amount of UVB-radiation produce immunosuppressive factors which, when administered in an effective amount to a subject mammal which is subsequently sensitized to a particular alloantigen, selectively suppress the DTH response in that mammal to that particular alloantigen. According to one preferred embodiment, the mammalian cells, preferably epidermal cells, are placed in suspension in a non-toxic, nutritive medium. While in suspension, the cells are irradiated with UV-radiation having a pre-determined wavelength. The source of the UV-radiation may be, for example, any commercially available "sunlamp," generating UV-radiation in pre-determined wavelengths. In one preferred embodiment, FS-40 sunlamps, Westinghouse (Bloomfield, N.J.) provided UVB-radiation. In another preferred embodiment, Dermalight 2001, (Dermalight. Systems, Studio City, Calif.) provided UVA-radiation. The UV-radiation administered to the cells must be sufficient to result in UV-irradiated cells which produce immunosuppressive factors. Preferably, the amount of radiation administered to the cells is from about 10 to about 100 J/m², and most preferably from about 10 to about 40 J/m². The immunosuppressive factors are preferably secreted by the cells into the nutritive media. The immunosuppressive factors are thereafter extracted from the UV-irradiated cells. This extraction step may simply be the process of separating the UV-irradiated cells from the nutritive media. However, any known separation technique can be employed in the practice of the inventive method. The immunosuppressive factors may also, prior to administration, be concentrated by techniques well known in the art. Thereafter, a therapeutically effective amount of the immunosuppressive factors are administered to a mammal. According to one preferred embodiment, the therapeutically effective amount of the immunosuppressive factors is determined by the subject's physician (or veterinarian if the subject is an animal) as that amount of immunosuppressive factor required to suppress the particular immune response to the particular alloantigen. Most preferably, however, the therapeutically effective amount is that amount which prevents the occurrence of a particular pathology related to a specific alloantigen. The administration of the immunosuppressive factors may be administered as a single or divided dose. The immunosuppressive factors are preferably administered by injection, for example, intraperitoneally, subcutaneously, intramuscularly or intravascularly. However, the immunosuppressive factors are most preferably administered by intravenous injection or infusion.

The subject mammal is thereafter sensitized to the particular alloantigen for which immunotolerance is sought. According to one preferred embodiment, epidermal cells derived from a skin graft comprise the alloantigen and are used to sensitize the subject mammal to produce immunotolerance to the later transplanted skin graft, generally referred to as an allograft. According to a second preferred embodiment, spleen cells are used to sensitize the subject mammal. In this embodiment the epidermal cells or the spleen cells (alloantigens) may have substantially identical antigenic profiles as the later transplanted graft (allograft).

The inventive methods of the present invention are directed toward treating or preventing an occurrence of an immunological-related pathology. In one embodiment, the immunological-related pathology is graft vs. host disease, or host vs. graft disease, e.g., transplant rejection.

In another embodiment, the immunological-related pathology is the DTH response to a particular alloantigen. In yet another embodiment, the immunological-related pathology is the CHS response to a particular antigen. In general, the immunological-related pathology is a pathological condition for which the suppression of a specific immune response to a particular alloantigen would be beneficial.

The immune response to allogeneic histocompatibility antigen s can be suppressed by injecting allogeneic spleen cells into mice that have been previously exposed to UV radiation. The suppression is mediated by antigen-specific suppressor T cells found in the spleens of the UV-irradiated mice. A previously unanswered question is, how does the irradiation of the animal's dorsal skin lead to the induction of splenic antigen specific suppressor cells? Findings of the present invention suggest that soluble factors released by UV-irradiated keratinocytes are involved in the induction of antigen-specific suppressor cells. Injection of culture supernatants from UV-irradiated keratinocytes into normal mice mimicked the effect of whole-body UV irradiation and suppressed the induction of delayed type hypersensitivity to alloantigen. Furthermore, spleen cells from these mice were unable to respond to the alloantigen in the mixed lymphocyte response. Antigen-specific suppressor T cells (Lyt 1+2−=, radiation resistant) were found in the spleens of the mice injected with suppressive supernatants. The production of the suppressive cytokine is not inhibited by indomethacin treatment of the keratinocytes, suggesting the prostaglandins are not involved. Inhibition of protein synthesis with cycloheximide or treatment of the supernatants from the UV-irradiated keratinocytes with trypsin removes all suppressive activity suggesting the active material is a protein since the suppression of the immune response to alloantigen induced by this suppressive cytokine mimics the suppression found after exposure to UV radiation, these findings support the concept the induction of systemic suppression by UV radiation results from the release of suppressive substances by UV-irradiated keratinocytes. In addition, these data also suggest the induction of antigen-specific suppressor cells by this factor (a glycoprotein being induced by UVB irradiation) may provide a novel method of suppressing allograft rejection.

The following examples are included to further describe the present invention and are not intended to limit the invention unless otherwise specifically indicated herein.

MATERIAL AND METHODS FOR EXAMPLES 1-3

Mice.

specific pathogen-free females C3H/HeN Cr (MTV—) and BALB/AnN mice were supplied by the NCI-Frederick Cancer Research Facility, Animal Production Area (Frederick, Md.) The animals were housed and cared for according to the guidelines set forth in The Guide For The Care And Use of Laboratory Animals, (DHHS Publication No. [NIH] 78-23), in a facility fully accredited by the American Association for the Accreditation of Laboratory Animal Care, and their use was approved by the Institution Animal Care and Use Committee.

Exposure Of Mice To UV Radiation.

The dorsal fur of the mice was removed by shaving with electric clippers. The mice were then exposed for 3 hrs. to UVB (280 nm–320 nm) radiation provided by a bank of 6 FS-40 sunlamps (Westinghouse, Bloomfield, N.J.). Approximately 70% of the radiation emitted by these lamps is within the UVB range. The irradiance of the source averaged 10 $W/m^2$, as measured by an IL-700 radiometer, using a PT171C UVB detector equipped with a UVB 320 filter and A127 quartz diffuser (International Light, Inc., Newburyport, Mass.). Due to shielding by the cage lids the incident dose received by the animals was approximately 4.5 $W/m^2$. The total dose of UV received was approximately 40 $kJ/m^2$. During irradiation the ears of the mice were covered with tape to prevent damage from the UV radiation.

In vitro UV-irradiation of epidermal cell cultures.

Epidermal cell suspensions were prepared from the ears and trunk skin of mice. The fur was removed by shaving and the skin was removed and cut into i $mm^2$ pieces. These were floated at 37° C. in 0.75% trypsin/EDTA. After 60 minutes the dermis was separated from the dermis by teasing apart with forceps. The epidermis was cut into small pieces and stirred for 30 minutes in 0.25% trypsin/EDTA. The resulting cell suspension was filtered through nylon mesh, counted and resuspended to $1 \times 10^6$ cell/ml in minimal essential media (MEM) supplemented with; 5% fetal calf serum, 2 mM glutamine and 1% non-essential amino acids (Gibco Laboratories, Grand Island, N.Y.). Five ml of the cell suspension was added to 100 mm tissue culture dishes. Twenty-four hours later the non-adherent cells were removed and the monolayers resuspended in PBS and irradiated with 200 $J/m^2$ of either UVA or UVB radiation. The source of the UVB radiation was a single FS-40 sunlamp with an output of 1.43 $W/m^2$, at a tube to target distance of 20 cm. This lamp emits a continuous spectrum from 270 nm to 390 nm with peaks at 313 nm and 365 nm. Approximately 70% of the energy emitted by this lamp was within the UVB region. The source of the UVA radiation was a Dermalight 2001 equipped with an optical filter (H-1) to remove contaminating UVB (Dermalight Systems, Studio City, Calif.). Essentially all the radiation (99.5%) emitted by this lamp was within the UVA range as determined with an optronics 742 Spectroradiometer (Optronic Laboratories Inc., Orlando, Fla.). The output of this lamp was 56 $W/m^2$ at a tube to target distance of 20 cm. Immediately after irradiation, the cells were washed 3 times with PBS and resuspended in serum free MEM. Eighteen to 24 hours later the supernatant (UVB-SN or UVA-SN) from the cultures was removed and passed through 0.22 micron filters. In some of the experiments the keratinocyte line, PAM 212 [19] was used. The cells were adjusted to $1 \times 10^6$ cells/ml and 5 ml of the cell suspension was plated in 100 mm tissue culture dishes. Twenty-four hours later these cells were irradiated as described above. The cells were resuspended in serum-free MEM and the supernatants obtained 18 to 24 hours later.

Control supernatants (NR-SN) were obtained from cells treated in an identical manner but not exposed to UV radiation.

Effect Of Supernatants From The UV-Irriadated Epidermal Cells On CHS.

Mice were injected via the tail vein with 0.5 ml of UVA-SN, UVB-SN or NR-SN. Five days later the animals were sensitized by the epicutaneous application of trinitrochlorobenzene (TNCB, 100 ul of a 3% w/v solution is acetone) or dinitrofluorobenzene (DNFB, 50 ul of a 0.3% v/v solution in acetone) on the shaved abdominal skin. Six days later the mice were challenged by applying 5 ul of a 1% solution of TNCB or a 0.2% solution of DNFB onto each ear surface. The thickness of the pinna of each ear was measured with a spring loaded micrometer (Swiss Precision Instruments, Los Angeles, Calif.) immediately prior to challenge and 24 hours later. The background response was determined by measuring the swelling found in animals that were not sensitized but were challenged. The specific swelling was calculated by subtracting the background swelling from that seen in the experimental groups. There were 5 mice per group.

Effect of supernatants from the UV-irradiated cells on DTH.

BALB/c mice were injected via the tail vein with 0.5 ml of UVB-SN, UVA-SN or the control, NR-SN. Five days later these mice were sensitized with allogeneic C3H spleen cells by injecting $2.5 \times 10^7$ cells into each flank. Six days later the mice were challenged with C3H spleen cells by injecting $10^7$ cells into each hind footpad. The resulting footpad swelling was read 24 hours later. As before, the background swelling was determined by challenging non-sensitized mice with C3H cells, and the specific swelling was calculated by subtracting the background swelling from the footpad swelling of the experimental groups. There were 5 mice per group.

Alternatively, BALB/c mice were sensitized with $5 \times 10^7$ syngeneic spleen cells modified with the trinitrophenol (TNP) hapten as described by Shearer [20]. Six days later these mice were challenged by injecting $10^7$ TNP-conjugated spleen cells into each hind footpad. Twenty-four hours later the footpad swelling was determined.

Determination of antibody production.

The slide modification [21] of the Jerne and Nordin [22] plaque assay was used. Mice were injected with 0.5 ml of UVB-SN, UVA-SN or NR-SN and 5 days later were immunized by the intravenous (iv) injection of a 1% solution of sheep erythrocytes (SRBC). Five days after immunization, the spleens of the mice were removed and the number of direct plaque-forming cells was determined by using SRBC or horse erythrocytes (HRBC) as the indicator cells.

Statistical Analysis.

A multiple comparison procedure employing a one way analysis of variance was used to determine statistical significant differences between experimental and control groups [23].

Probabilities less than 0.05 were considered significant.

Representative experiments are shown; each experiment was repeated at least twice with similar results.

EXAMPLE 1

SUPPRESSION OF DTH BUT NOT CHS AFTER THE INJECTION OF SUPERNATANTS FROM UVB-IRRADIATED EPIDERMAL CELLS

Primary epidermal cell cultures were prepared from the back skin and ears of C3H mice. The cultures were exposed to 200 J/m2 of UVB radiation and 24 hours later the supernatants from these cultures were injected into normal mice. Five days later half of the mice were sensitized with TNCB and the other half injected with Balb/c spleen cells. Six days later the mice were challenged with the respective antigen and the cHs and DTH response measured 24 hours later. As controls for the experiment, two groups of mice were also irradiated with 40 kJ/m² of UVB-radiation (whole body irradiation). As can be seen in FIG. 1, exposure to whole-body UVB radiation (UVB) suppressed both the generation of CHS (panel A) and DTH (panel B) when compared to the non-irradiated control (NR, $P<0.001$). The injection of the UVB-SN also suppressed DTH (FIG. 1B). Contrary to expectations, the injection of the UVB-SN had no significant effect on CHS (FIG. 1A). The injection of the control supernatant (NR-SN) had no suppressive effect on CHS or DTH.

Figure 2B:
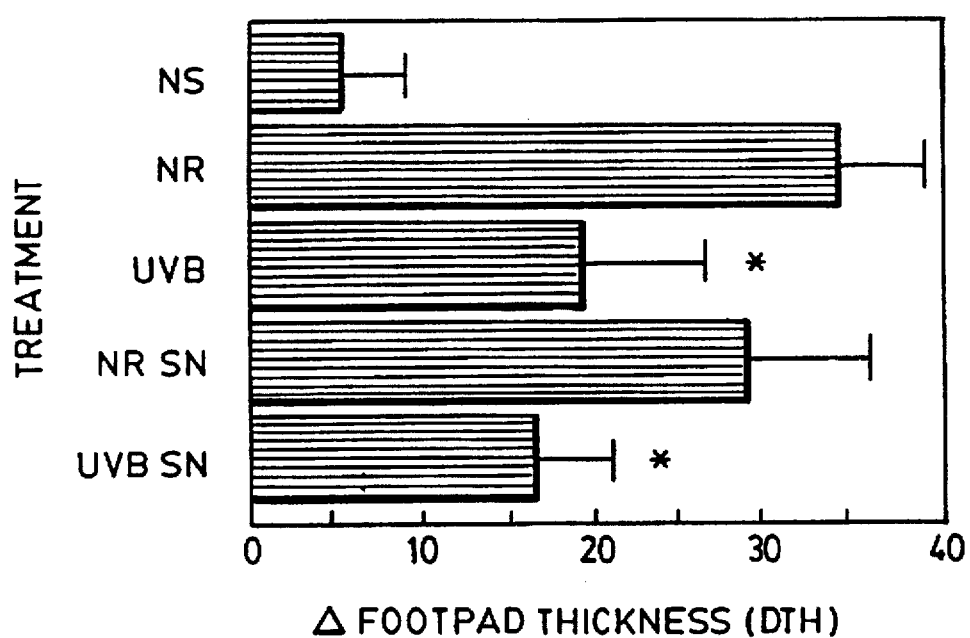

A keratinocyte line, Pam 212, was also used as a source of potentially immunosuppressive supernatants. The effect that the injection of these supernatants had on the generation of CHS and DTH is shown in FIG. 2 (A and B). As before, the control for this experiment consisted of exposing mice to 40 mJ/m² of UVB radiation. There was a significant suppression ($P<0.001$) of both CHS and DTH after whole-body UVB radiation (UVB) when compared to the immune response generated in unirradiated animals (MR). When the UVB-SN was injected into BALB/c mice that were subsequently sensitized with TNCB, it had no suppressive effect (FIG. 2A). When, however, the same UVB-SN was injected into BALB/c mice that were subsequently injected with C3H spleen cells, DTH to the alloantigen was significantly suppressed ($P<0.001$) (see FIG. 2B). The injection of supernatants from non-irradiated Pam 212 cells (NR-SN) had no suppressive effect. This experiment was repeated using two other contact allergens, dinitrofluorobenzene and oxazofone. In both cases the UVB-SN, generated by irradiating Pam 212 cells with UVB radiation had no suppressive effect on CHS.

Figure 3:
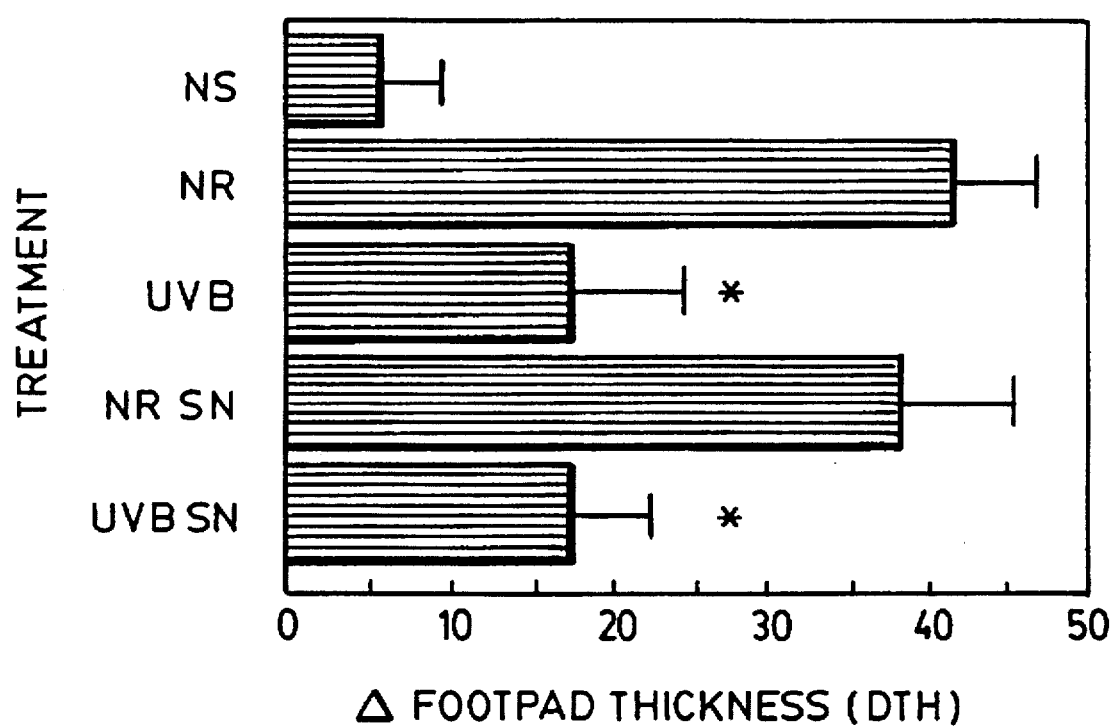
FIG. 3 shows the effect of the supernatants from UVB-irradiated Pam 212 cells on the induction of DTH to TNP-conjugated syngeneic spleen cells. Mice were injected with supernatants from the UVB-irradiated (UVB-SN) or control (NR SN) keratinocyte cell cultures or exposed to 40 kJ/m$^2$ of UV radiation (UV). The asterisk indicates a significant difference (P<0.001) from the response observed in the positive control (MR). The background response was measured in mice that were challenged but not sensitized with the TNP-conjugated normal spleen cells (NS). There were 5 mice/group: units=cm×10$^{-3}$.

The above data demonstrated that the immunosuppressive factors generated from the UVB-irradiated epidermal cells suppress DTH but not CHS. The effect that injection of UVB-SN had on the DTH response to a different antigen was also examined. TNP-conjugated syngeneic spleen cells were used as the antigen. Supernatants from UVB-irradiated and non-irradiated Pam 212 cells were injected into Balb/c mice. These mice were then sensitized and challenged with TNP-conjugated Balb/c spleen cells. The data from this experiment is summarized in FIG. 3. Compared to the non-irradiated control (NR), both the injection of the UVB-SN and exposure of the mice to whole-body UVB-radiation (UVB), resulted in a significant ($P<0.001$) suppression of DTH to TNP-modified spleen cells. This data indicated that, regardless of the antigen used, supernatants generated by exposing epidermal cells to UVB suppress DTH but not CHS.

Contrary to the results published by Schwarz and colleagues, the supernatant released from UVB-irradiated epidermal cells was unable to suppress CHS. In Schwarz et al. [15] the source of the UVB-radiation used was an Osram Vitalux bulb emitting a continuous spectrum between 300 nm and 600 nm, with peaks at 310 nm and 390 nm. The FS-40 lamp used in the present invention has a continuous spectrum of from about 270 nm to 390 nm, with peaks at 312 nm and 365 nm. Thus, Schwarz and colleagues appear to have used a considerable amount of UVA in the generation of their suppressor factor and, as demonstrated herein, UVA-radiation of cells generated a factor which selectively suppresses CHS while UVB-radiation generates a factor that selectively suppresses DTH.

EXAMPLE 2

SUPPRESSION OF CHS BUT NOT DTH BY FACTORS RELEASED FROM UVA-IRRADIATED KERATINOCYTES

Separate Pam 212 cultures were irradiated with 200 J/m² of either UVB or UVA radiation. Twenty-four hours later, 0.5 ml of each supernatant as well as 0.5 ml of the control supernatant from non-irradiated cultures was injected into various groups of mice. Five days later one half of the mice were sensitized with DNFB and the other half were injected with allogeneic spleen cells. Six days after sensitization the mice were challenged with the appropriate antigen and the resulting DTH and CHS reactions were measured one day later. The data from this experiment are summarized in Table 1.

TABLE 1

EFFECT OF SUPERNATANTS FROM UVA AND
UVB-IRRADIATED PAM 212 CELLS ON CHS AND DTH

|     | Treatment | Ear[b] Thickness (± SEM) | Specific[c] Swelling | %[d] Suppression | P[e] |
|-----|-----------|--------------------------|----------------------|------------------|------|
| CHS | None      | 3 + 1                    | 0                    | —                | —    |
|     | NR        | 16 + 4                   | 13                   | 0                | —    |
|     | NR-SN     | 14 + 6                   | 11                   | 15               | NS   |
|     | UVA-SN    | 9 + 2                    | 6                    | 54               | 0.002|
|     | UVB-SN    | 12 + 3                   | 9                    | 31               | NS   |

|     | Treatment[a] | foot pad[b] thickness (± SEM) | specific[c] Swelling | %[d] Suppression | P[e] |
|-----|--------------|-------------------------------|----------------------|------------------|------|
| DTH | None         | 3 + 3                         | 0                    | —                | —    |
|     | NR           | 31 + 5                        | 28                   | 0                | —    |
|     | NR-SN        | 29 + 7                        | 26                   | 8                | NS   |
|     | UVA-SN       | 25 + 5                        | 22                   | 21               | NS   |
|     | UVB-SN       | 19 + 3                        | 16                   | 43               | 0.002|

[a]Mice were injected with 0.5 ml of supernatant from Pam 212 cultures exposed to 200 J/m$^2$ of UVA (UVA-SN) or UVB (UVB-SN) radiation, or with 0.5 ml of supernatant from non-irradiated cells (NR-SN). The response in these mice was compared to the response of the control animals (NR). In the CHS experiment the mice were sensitized with DNFB, in the DTH experiment the mice were injected with allogeneic spleen cells.
[b]Units - cm × 10$^{-3}$; 5 mice per group.
[c]The background swelling found in the non-sensitized control mice was subtracted from the swelling found in the experimental groups.
[d][1 − (specific swelling of experimental group/specific swelling of control group)] × 100.
[e]P values were determined by a one way ANOVA: NS = not significantly different from the NR control (P > 0.05)

As before, the injection of supernatants from the non-irradiated cells (NR-SN) had no significant effect on the magnitude of the CHS response (compare normal mice (MR) to NR-SN, P>0.05). While the injection of the supernatant from the UVB-irradiated Pam 212 cells (UVB-SN) resulted in a minimal level of CHS suppression there was no significant difference between these two groups (NR vs UVB-SN, P >0.050). However, when the supernatant from UVA-irradiated cells (UVA-SN) was injected into mice there was a significant suppression of the CHS response (NR vs UVA-SN, P <0.002).

The opposite situation was observed when DTH was measured. The DTH response found after the injection of the supernatant from the non-irradiated cells (NR-SN) or the supernatant from the UVA-irradiated cells (UVA-SN) was indistinguishable from the control (NR vs MR-SN and NR vs. UVA-SN, P>0.05). But as shown previously, the injection of the supernatant from the UVB-irradiated Pam 212 cells (UVA-SN) resulted in a significant suppression of the DTH response to the alloantigen (NR vs UVB-SN, P<0.002). This data demonstrated that at least two factors are released from UV-irradiated keratinocytes, one triggered by UVA radiation that suppresses CHS and the second, triggered by UVB radiation, that suppresses DTH.

EXAMPLE 3

EFFECT OF UVB-SN ON ANTIBODY PRODUCTION

Mice were injected with the UVB-SN produced as described in Example 2 or exposed to 40 kJ/m$^2$ of UVB-radiation. Five days later they were injected with 0.1 ml of a 1% solution of SRBC via the tail vein. Five days after this immunization, their spleens were removed and the numbers of antibody-forming cells were determined. This experiment is summarized in Table 2.

TABLE 2

EFFECT OF THE SUPERNATANT FROM UVB-IRRADIATED
PAM 212 CELLS ON ANTIBODY FORMATION

| Treatment[a] | Anti-SRBC PFC/10$^6$ spleen cells[b] (± SEM) |
|--------------|------------------------------------------------|
| + HRBC       | 0                                              |
| + SRBC       | 1144 + 90                                      |
| UVB + SRBC   | 1052 + 42                                      |
| UVB-SN − SRBC| 1081 + 78                                      |
| NR-SN + SRBC | 1317 + 68                                      |

[a]Mice were exposed to 40 kJ/m$^2$ of UV radiation (UVB) or injected with supernatant from UVB-irradiated primary epidermal cell cultures (UVB-SN) or supernatant from the non-irradiated control (NR-SN). These mice were then injected with sheep erythrocytes. The number of plaque forming cells. (PFC) was determined by using SRBC as the indicator cells. The response of normal mice immunized with sheep erythrocytes. (+SRBC), was compared to the response found in mice exposed to UVB or injected with supernatants from the epidermal cell cultures. The background response was determined by injecting mice with horse erythrocytes (+ HRBC) and measuring the number of anti-SRBC plaques.
[b]There were 2 mice per group. Each spleen was assayed individually, 3 slides per spleen. The data represents the mean values from six slides.

There was no significant effect on antibody formation by either total-body exposure to UVB-radiation, or injection of the UVB-SN suppressive supernatants. This demonstrated that the suppression induced by the immunosuppressive factor, like the suppression induced by total body exposure to UVB radiation, is selective.

MATERIALS AND METHODS FOR EXAMPLES
4–9

Mice.

Pathogen-free female C3H/HEN (MTV-) BALB/c and C57BL/6 mice were obtained from the National Cancer Institute, Frederick Cancer Research Facility Animal Production Area. The mice were cared for according to the guidelines set forth in the Guide for the Care and Use of Laboratory Animals (DHHS Publication No. [NIH] 78-23) in an AAALAC accredited animal facility and their use was approved by the Institutional Animal Care and Use Committee.

Treatment of mice with UVB-radiation.

Mice were exposed to UVB (280–320) radiation provided by a bank of 6 FS-40 sunlamps (Westinghouse, Bloomfield, N.J.). The spectral output of the FS-40 bulbs as well as the method used to irradiate the mice have been described in detail in the Materials and Methods for Examples 1–3.

Effect of UVB on allograft rejection.

Recipient BALB/c mice were irradiated with 40 kj/m$^2$ on day 0. During the irradiation their eats were covered with tape to prevent damage. Five days later, the mice were sensitized with antigen by injecting 5×10$^7$ C3H spleen cells subcutaneously. One week later, C3H heart fragments were implanted into the ears of the recipient mice according to the procedure of Klein et al. (25). Survival of each graft was scored by visual examination of pulsating tissue. Grafts were first scored at 5 days (at which time 100% were viable), and then scored every 2–3 days afterward.

Induction of Graft versus Host Disease (GVHD).

GVHD was induced by using the procedure of Korngold and Sprent (26). Lethally X-irradiated (850 rads) BALB/c mice were reconstituted with $5\times10^6$ T cell-depleted C3H bone marrow cells (ATBM, antiThy 1.2 clone 30-H12, Becton Dickinson, Mountain View, Calif., plus complement) and $5\times10^5$ C3H spleen cells. Spleen cells were obtained from normal C3H mice, C3H mice exposed to 40 kJ/m² UVB, C3H mice exposed to UVB and sensitized with $5'10^7$ BALB/c spleen cells 5 days after UVB exposure, and C3H mice sensitized with $5\times10^6$ BALB/c cells. Spleen cells and allogeneic T cell- depleted bone marrow (ATBM) were injected into the recipient mice via the tail vein. The recipient BALB/c mice were maintained on autoclaved food, bedding, and antibiotic-supplemented water. The animals were checked daily for morbidity and mortality.

Effect of UVB on tumor allograft rejection.

C3H mice were exposed to 40 kJ/m² of UVB-radiation, and 5 days later sensitized by the subcutaneous injection of $5\times10^7$ mitomycin C-treated (50 ug/ml) B16 melanoma cells (27). One week later, these mice were challenged with $2\times10^6$ VIABLE B16 CELLS. At the same time, one group of normal c57BL/6 mice was challenged with an equivalent number of B16 cells. In addition, BALB/c mice were also exposed to UVB and sensitized with $5\times10^7$ mitomycin C-treated UV2237 cells (a progressor UV-induced tumor generated in C3H mice (28)). One week after sensitization, the mice were challenged with $2\times10^6$ viable UV2237 cells. As a control normal, C3H mice were also injected with two million UV2237 cells.

Mixed lymphocyte cultures.

Spleen cells were removed from C3H mice that were exposed to UVB and sensitized with BALB/c cells or from nonirradiated mice that were sensitized with BALB/c cells and single-cell suspensions were prepared. Erythrocytes were lysed with ammonium chloride and the cells were washed and resuspended in RPMI1640 medium (31). Generally, $2\times10^5$ gamma-irradiated (5000 rads) stimulator cells were incubated in 96-well round-bottomed microliter plates. The cells were cultured for 5 days at 37° C., during the last 6 hrs of culture, 1 uCi/well of tritiated thymidine (ICN Radiochemicals, Irvine, Calif.) was added. The incorporation of the radioisotope by the responder cells was measured by harvesting the cells onto glass fiber filters, followed by liquid scintillation counting.

Depletion of lymphocyte subsets by monoclonal antibody and complement treatment.

The methods used to deplete lymphocyte subsets with specific monoclonal antibodies and complement have been described (29, 30). The antibodies used were: anti-Thy 1.2 (clone 30-H12, Becton Dickinson, Mountain View, Calif.), anti-Lyt-1 and Lyt-2 (New England Nuclear, Boston, Mass.), anti-L3T4a (clone GK-15), and anti-IJ$^k$ (clone WF8c.12.8). The anti L3T4a and anti I-J$^k$ were obtained from the Dept. of Immunology, M. D. Anderson Hospital, Houston, Tex.

EXAMPLE 4

RELATIONSHIP BETWEEN EXPOSURE TO UVB AND RESULTING IMMUNOSUPPRESSION

Figure 4:
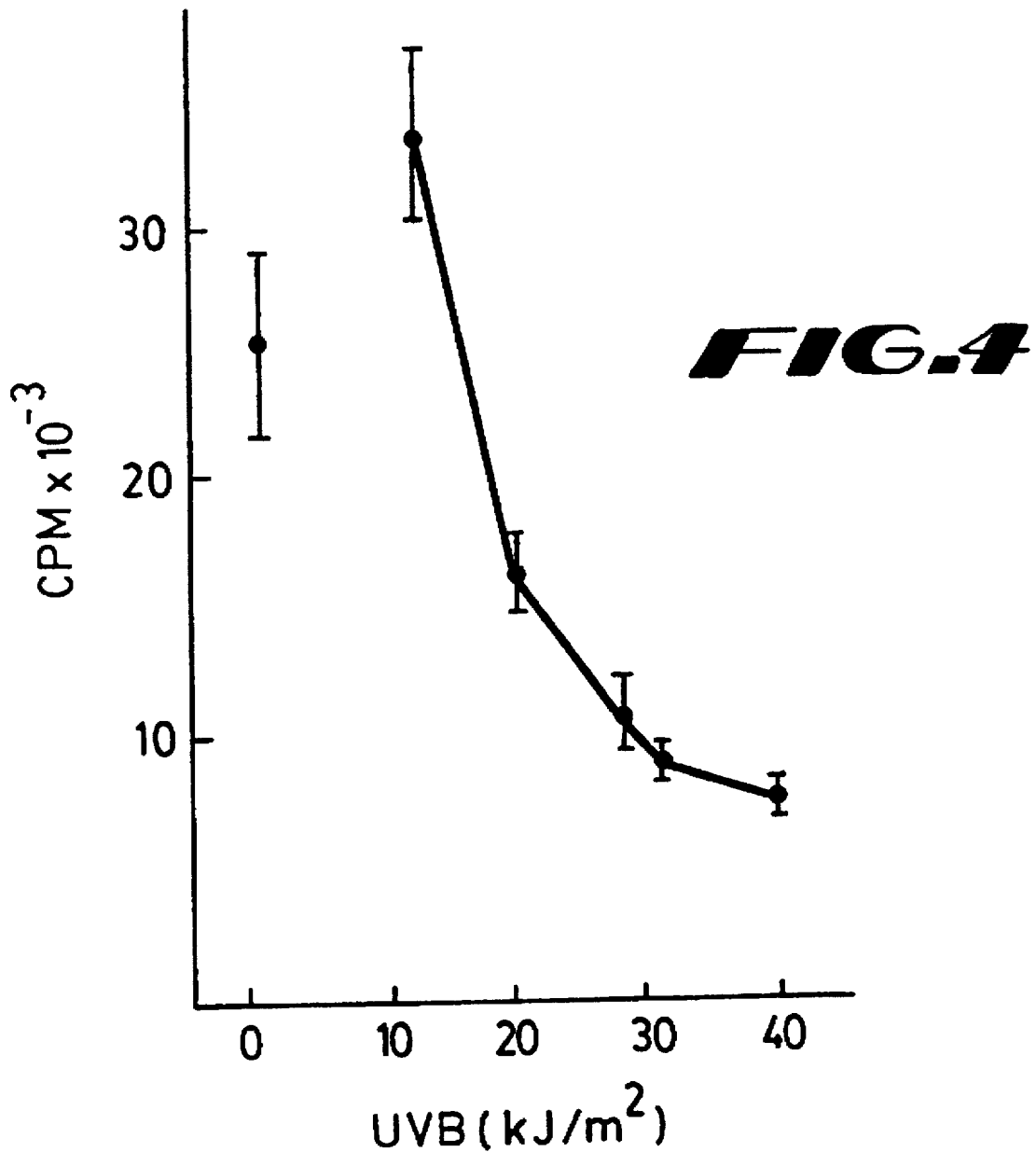
FIG. 4 shows the relationship between the suppression of MLR and the dose of UVB given. Mice wire exposed to various doses of UVB and sensitized with 5×10$^7$ allogeneic cells. Cells from these mice were cultured in an MLR, and their response was compared with the response observed when cells were isolated from nonirradiated antigen-sensitized mice.

FIG. 4 shows the relationship between the dose of UV given and the resulting suppression. The proliferation of spleen cells taken from C3H mice that were exposed to various doses of UVB and then sensitized with alloantigen was measured. This proliferation was compared with the response observed when spleen cells were isolated from C3H mice that were not exposed to UVB but were sensitized with alloantigen. The data presented in FIG. 4 demonstrate that, as the dose of UVB given was decreased, the resulting suppression decreased. This showed a direct relationship between the degree of suppression and the exposure to UVB. Based on these data, a 40 kJ/m² exposure to UVB was used in the following experiments.

EXAMPLE 5

EFFECT OF EXPOSURE TO UVR ON THE REJECTION OF ALLOGENEIC HEART GRAFTS

Recipient BALB/c mice received one of 4 treatments. The first group was the normal control, the second group was exposed to UVB, the third group was exposed to UVB and sensitized with C3H spleen cells, and the fourth group was the nonirradiated (NR) control that had been sensitized with C3H spleen cells. Seven days after sensitization, newborn C3H heart fragments (allografts) were implanted in the left ears of the BALB/c mice. As demonstrated in Table 3 there was a significant prolongation of graft survival in mice exposed to UVB and sensitized with alloantigen (P<0.001, Wilcoxon rank sum test).

TABLE 3

PROLONGATION OF ALLOGRAFT SURVIVAL AFTER UVB TREATMENT AND ANTIGENIC SENSITIZATION OF THE RECIPIENT

| Treatment of recipient | Survival of heart grafts* | |
|---|---|---|
|  | MST (days) | RANGE |
| control | 5 | 5–7 |
| UVB | 5 | 5–7 |
| UVB + C3H spleen cells | 14** | 7–28 |
| C3H spleen cells | 5 | 5–7 |

*Survival of each graft was scored by visual examination of pulsating tissue using a stereomicroscope at 10 × magnification. Grafts were first scored at 5 days and then scored every 2–3 days afterward. Control BALB/c heart fragments were implanted into each right ear; an MST of >days was observed. There were 10 mice in each group.
**P < .001, Wilcoxon rank-sum test.

Exposure of the recipients to UVB alone, or sensitization with the allantigen only, did not prolong the survival of the allografts when compared with the normal control. As an additional control for this experiment, BALB/c hearts were placed into the right ears of these mice the median survival time (MST) of these grafts was greater than 60 days.

EXAMPLE 6

THE SPECIFICITY OF UVB SUPPRESSION

C57BL/6 mice were exposed to UVB and sensitized with either BALB/c or C3H spleen cells. Seven days after sensitization a BALB/c heart fragment (allograft was implanted into one ear and a C3H heart fragment was implanted into the other. The survival of the allografts was compared with the mean survival time (MST) of heart fragments transplanted into a normal animal. The results from this experiment, as summarized in Table 4, demonstrate that allograft survival is prolonged only when the allograft is syngeneic to the antigen used to sensitize the UV-irradiated animal.

TABLE 4

SPECIFICITY OF THE SUPPRESSION OF ALLOGRAFT REJECTION[a]

| Treatment of recipients | Survival of heart grafts (MST [range]) | |
|---|---|---|
| | BALB/c | C3H |
| UVB + BALB/c | 14 (14–21)[b] | 5(5–7) |
| UVB + C3H | 1 (5–1) | 14(7–21)[b] |
| None | 5 (5–7) | 5(5–7) |

[a]Recipient C57BL/6 mice were exposed to UVB radiation and sensitized with either BALB/c or C3H spleen cells. At one week following sensitization C3H heart fragments were implanted in the left ear and BALB/c heart fragments were implanted in the right ear. There were five mice in each group.
[b]$P < .001$ vs. the normal controls.

EXAMPLE 7

SUPPRESSION OF TUMOR ALLOGRAFT REJECTION BY UVB AND ALLOANTIGENIC SENSITIZATION

Another measure of the immune response to alloantigens is the ability to reject tumor allografts. The effect that UVB and alloantigenic sensitization had on tumor allograft rejection was measured by the following experiment. The mice were separated into four groups, the normal control, UVB-irradiated only, UVB-irradiated and sensitized with alloantigen, and alloantigen sensitized only. These mice were then challenged with the allogeneic tumors. As demonstrated in Table 5, the allogeneic tumors were all rejected by the normal mice.

TABLE 5

SUPPRESSION OF TUMOR ALLOGRAFT REJECTION BY THE ANTIGENIC SENSITIZATION OF UV IRRADIATED MICE

| Treatment of recipients C3H | | Tumor incidence | Treatment of recipients BALB/c | | Tumor incidence |
|---|---|---|---|---|---|
| UVB[a] | Sensitization[b] (B16) | | UVB[a] | Sensitization[c] (UV2237) | |
| – | – | 0/5 d | – | – | 0/10[d] |
| + | – | 0/5 | + | – | 0/10 |
| – | B16 | 0/5 | – | UV2237 | 0/10 |
| + | B16 | 4/5 | + | UV2237 | 6/10[e] |

[a]Mice were exposed to 40 kJ/m² of UVB on the shaved dorsal skin.
[b]$5 \times 10^7$ mitomycin C-treated B16 cells, 5 days after irradiation.
[c]$5 \times 10^7$ mitomycin C-treated UV2237 cells, 5 days after irradiation.
[d]$5 \times 10^7$ mitomycin C-treated UV2237 cells, 5 days after irradiation.
[e]$P < .01$ vs nonirradiated sensitized mice, chi-square test; 100% of normal C57BL/6 control mice injected with B16 and 80% of normal; C3H control mice injected with UV2237 developed tumors.

Treatment with UVB only or alloantigenic Sensitization only had no effect on tumor rejection. However, when the mice were first exposed to UVB and then sensitized with the tumor alloantigen, the rejection of the tumors was suppressed, as evident by tumor growth in the allogeneic mice. To rule out the possibility that these results were due to the selection of antigenless variants, the tumors were excised and transplanted into normal mice. The B16 grew progressively in C57BL/6 mice but was rejected in C3H mice. Similarly, the UV 22327 grew in normal C3H mice but was rejected in normal BALB/c mice.

EXAMPLE 8

THE EFFECT OF UVB AND ALLOANTIGENIC SENSITIZATION ON GVHD

The ability of UVB and alloantigenic sensitization to effect the survival of mice with lethal GVHD was examined. GVHD was induced by injecting lethally X-irradiated BALB/c mice with a mixture of T cell-depleted C3H bone marrow cells and mature C3H spleen cells (26). The question addressed was whether treatment of the spleen cell donors with UVB followed by alloantigenic sensitization could induce a state of suppression that would inhibit the reaction of the graft against the host. The donor mice received one of four treatments, the normal control, UVB only, UVB plus alloantigenic sensitization, and sensitization only. Seven days after sensitization, spleen cells from these mice plus allogenic T-cell depleted bone marrow (ATBM) were injected into the BALB/mice. As shown in FIG. 5, when the BALB/c mice were reconstituted with ATBM only, an MST greater than 90 days was observed. Injection of normal spleen cells with the ATBM resulted in the induction of GVHD with an MST of 12 days. The use of spleen cells from mice exposed only to UVB (UVB spleen cells) or from mice sensitized only with antigen (sensitized UVB spleen cells) did not alter the MST. When, however, the spleen cells were obtained from C3H mice that were first exposed to UVB and then sensitized with BALB/c cells (sensitized UVB spleen cells), a significant prolongation of the MST was observed.

A major problem in bone marrow transplantation is the induction of GVHD. Methods of reducing GVHD generally include histocompatibility matching between the donor and recipient, the use of immunosuppressive drugs, and the removal of T cells from the graft (24). Using a method of the present invention a significant prolongation of survival was achieved when spleen cells from UVB-irradiated antigen-sensitized mice were transferred to recipients that differed across major histocompatibility barriers, in the absence of any immunosuppressive drugs. The methods of the present invention yield another method of reducing the incidence of GVHD.

EXAMPLE 9

UV-INDUCED SUPPRESSOR CELLS ARE RESPONSIBLE FOR THE SUPPRESSION OF THE IMMUNE RESPONSE TO ALLOANTIGENS

The present inventor has previously shown that antigen-specific suppressor cells (possibly T-lymphocytes) are present in the spleens of the ultraviolet-irradiated alloantigen sensitized mice (31). To establish identity of these suppressor cells, cells from the UV-treated antigen-sensitized mice were treated with anti-Thy 1.2 plus complement prior to adding them to a primary mixed lymphocyte reaction (MLR). As demonstrated by the data presented in Table 6, depletion of T cells from the suppressor cell population totally abrogated the suppressive effect.

TABLE 6

PHENOTYPE OF SPLEEN CELLS FROM UVB-TREATED MICE THAT SUPPRESS MLR

| Cells cultured[a] | CPM ± SEM[b] | %[c] Suppression | p[d] |
|---|---|---|---|
| C3H | 4,176 ± 1571 | | |
| C3H + BALB/c | 99,444 ± 7130 | 0 | |

TABLE 6-continued

PHENOTYPE OF SPLEEN CELLS FROM
UVB-TREATED MICE THAT SUPPRESS MLR

| Cells cultured[a] | CPM ± SEM[b] | %[c] Suppression | p[d] |
|---|---|---|---|
| C3H + BALB/c + UVB | 20,251 ± 1288 | 80 | <.001 |
| C3H + BALB/c + NR | 102,703 ± 9017 | 0 | |
| C3H + BALB/c + aThy1.2UVB | 167,249 ± 26,073 | 0 | |
| C3H + BALB/c + aLyt1.1UVB | 135,026 ± 15,323 | 0 | |
| C3H + BALB/c + aLyt2.1UVB | 20,237 ± 3192 | 80 | <.001 |
| C3H + BALB/c + aIJ$^k$UVB | 102,529 ± 7303 | 0 | |
| C3H + BALB/c + aL3T4UVB | 112,043 ± 4687 | 0 | |
| C3H + BALB/c + aIgGUV | 55,358 ± 318 | 45 | <.002 |

[a] $2 \times 10^5$ C3H cells plus $2 \times 10^5$ mitomycin C-treated BALB/c cells were cultured with $2 \times 10^5$ nylon wool-purified spleen cells from UV-treated or NR control mice.
[b] Means values from triplicate cultures ± SEM.
[c] (1 − [CPM C3H + BALB/c + UVB cellS/CPM C3H + BALB/c]) × 100.
[d] p value determined by two-tailed Student's t test; C3H + BALB/c vs. C3H + BALB/c + UVB cells.

In addition, depletion of Lyt 1+IJ$^{k+}$ and L3T4a$^+$ cells also removed the suppressive effect but depletion of Lyt 2$^+$ or Ig$^+$ cells had no effect. These data demonstrate that the suppressor cells induced by alloantigenic sensitization of UVB-irradiated mice are indeed T-cells.

EXAMPLE 10

SUPPRESSION OF THE IMMUNE RESPONSE TO ALLOANTIGEN BY FACTORS RELEASED FROM UV-IRRADIATED KERATINOCYTES

Exposure of mice to UV radiation followed by injection of allogeneic cells results in suppression of the immune response to alloantigen. Both the induction of delayed hypersensitivity (DTH) and the ability of spleen cells from UV-irradiated alloantigen-sensitized mice to proliferate to alloantigen in the mixed lymphocyte reaction (MLR) is suppressed (6). The suppression is specific, sensitization of C3H mice with BALB/c cells after exposure to UV radiation suppresses the response of the C3H mice against BALB/c antigens, but the response of these mice against other alloantigens, such as C57B1/6 (B6) is not suppressed. Antigen-specific Thy 1.2+, Lyt 1+, 2- suppressor cells are found in the spleens of these mice. Two signals are required to induce the suppressor cells, the mice must be exposed to UV radiation and sensitized with alloantigen. Exposure to UV radiation alone or simple antigenic sensitization is not sufficient to induce suppression. Allograft rejection is also suppressed in mice exposed to UV and sensitized with alloantigen (32). The ability to reject allogeneic heart fragments is significantly suppressed by treating the recipient mice with UV radiation. Here, also the suppression is specific, exposure of BALB/c mice to UV followed by injection of C3H spleen cells results in a prolonged survival of C3H heart fragments but not B6 heart fragments. The survival of the B6 hearts was similar to the survival found in non-irradiated normal controls. In addition, the ability of spleen cells from mice exposed to UV and sensitized with alloantigen to induce lethal graft versus host disease in x-irradiated allogeneic recipient mice was significantly suppressed (32). these data demonstrate that UV exposure can be used to suppress the rejection of organ transplants. The major advantage in using UV exposure coupled with allogeneic sensitization to induce suppression is the antigen-specificity of the resulting suppressor cells.

An intriguing and not completely understood question about the suppression induced by UV-radiation is: how are suppressor T cells induced? Clearly, the penetrating power of UV radiation is not sufficient to directly irradiate the cells of the spleen (33). One hypothesis is that a soluble photoproduct is released by the UV-irradiated epidermal cells that leads to the development of suppressor cells. This hypothesis is supported by a number of recent studies. DeFabo and Noonan (10) have suggested that UV-irradiation of the skin results in the isomerization of urocanic acid (trans to cis) which may play a role in the induction of suppressor cells. Ross et al. (34) subsequently demonstrated the injection of cis-urocanic acid into normal mice could induce antigen-specific suppressor cells. Swartz (8) found that when serum from UV-irradiated mice was injected into normal animals, their ability to respond to contact allergens was significantly depressed. Experiments by Robertson et al. (13) demonstrated that the intravenous injection of IL-1 could mimic the effect of UV and cause suppression of CHS. This effect was overcome by indomethacin, suggesting a possible role for prostaglandins. Since IL-1 is released into the serum of mice after UV irradiation, Gahring et al. (14) suggested that the severe phototoxicity resulting from UV exposure may cause the release of IL-1 into the circulation and be responsible for the down regulation of CHS. Direct evidence for the release of cytokines from UV-irradiated epidermal cells comes from Schwarz et al. (35, 36) who found that in vitro irradiation of epidermal cell cultures caused the release of a soluble mediator into the culture supernatant. Injection of the culture supernatants into mice could mimic the effect of whole-body UV-irradiation and suppress the development of CHS. Furthermore, a 40 kilodalton molecule isolated from the suppressive supernatant inhibited the ability of IL-1 to stimulate thymocyte proliferation. The addition of indomethacin to the epidermal cell cultures did not affect the generation of the suppressive supernatant, suggesting a different mechanism from that described by Robertson et al. (13).

A question that is addressed in this Example is: can the injection of supernatants from UV-irradiated keratinocytes followed by alloantigenic sensitization induce alloantigen-specific Ts? The data demonstrate here that a soluble product from UV-irradiated keratinocytes can mimic the effect of total body exposure to UV radiation and suppress DTH and MLR to alloantigen. Antigen-specific suppressor T cells are found in the spleens of the animals injected with the supernatants from the UV-irradiated keratinocytes. These data suggest the suppressive cytokines released from UV-irradiated keratinocytes may play a role in the induction of antigen-specific suppressor T cells after exposure to UV radiation. Furthermore, these data suggest that the use of factors released from UV-irradiated keratinocytes should provide a novel approach of suppressing the rejection of organ transplants.

Materials and Methods for Example 10

Animals

Specific-pathogen-free female C3H/HeN, BALB/c, and C57B1/6 mice were obtained from the Animal Production Area, Frederick Cancer Research Facility, Frederick, Md. The animals were housed and cared for according to the guide for the care and use of laboratory animals (DHHS publication # (NIH) 78-23), and their use was approved by the institutional animal care and use committee.

Exposure of mice to UV radiation

The method used has been described in detail elsewhere (6). the dorsal skin of the mice was shaved and the animals were exposed to UVB (280 nm–320 nm) radiation provided by a bank of six FS-40 sunlamps (Westinghouse, Bloomfield, N.J.). The total dose received by the mice during a 3 hr exposure was 40 kJ/m$^2$.

In vitro UV-irradiation of epidermal cell cultures

The procedure of Schwarz et al. (35) was used to irradiate epidermal cell cultures. Five million Pam 212 cells (kindly provided to us by Dr. Stuart Yuspa, National Cancer Institute) were added to 100 mm tissue culture dishes in minimum essential medium (MEM) supplemented with 10% fetal calf serum and cultured overnight. The medium was removed and the cells were resuspended with phosphate-buffered saline (PBS). The monolayers were then exposed to 200 J/m$^2$ of UVB radiation. The source of the radiation was a single FS-40 sunlight bulb (Westinghouse, Bloomfield, N.J.), with an output of 1.43 W/m$^2$, at a tube to target distance of 20 cm. After irradiation the cells were washed 3 times with PBS and resuspended in serum-free MEM. Twenty-four hours later the supernatants were removed and passed through a 0.2 micro-M filter. The protein concentration was determined by the Bradford assay (Bio-Rad, Rockville Centre, N.Y.). Approximately 5 to 10 micrograms of protein was injected into each mouse. Control supernatants were obtained from Pam 212 cells handled in a similar manner but not exposed to UV radiation. Endotoxin contamination was below the limit of detection (0.125 ng/ml) as determined by the Limulus amebocyte lysate assay (Cape Cod Associates, Woods Hole, Mass.).

Effect of supernatants from UV-irradiated epidermal cells on DTH to alloantigens C3H or BALB/c mice were injected i.v. with 0.5 ml of the supernatants from UV-irradiated Pam 212 cells or with 0.5 ml of control supernatants. Five days later the mice were immunized by a subcutaneous injection of 5×10$^7$ allogeneic spleen cells. Six days later the mice were challenged by injecting 10$^7$ allogeneic spleen cells into each hind footpad. The footpad swelling was measured 24 h later with an engineer's micrometer (Swiss Precision Instruments, Los Angeles, Calif.). The background response was calculated from the footpad swelling found in non-immunized mice. The specific footpad swelling was determined by subtracting the background response from the response found in the immunized mice.

Adoptive transfer of suppressor cells

Spleens were removed from mice that had a suppressed DTH response. Single-cell suspensions were prepared and 10$^8$ cells were injected into the tail veins of syngeneic recipient mice. Immediately after the cell transfer these mice were immunized with 5×10$^7$ allogeneic spleen cells. Six days later the mice were challenged as described above. The immune response to the allogeneic spleen cells Was determined by measuring the animal's footpad swelling 24 hours later.

Effect of supernatants from UV-irradiated cells on the Mixed Lymphocyte Response (MLR)

C3H mice were injected i.v. with 0.5 ml (5 to 10 micrograms of protein) of supernatants from the UV-irradiated Pam 212 cells. Five days later the mice were immunized by a subcutaneous injection of 5×10$^7$ B6 spleen cells and, seven days later, their spleens were removed and single-cell suspensions prepared. The responder cells were resuspended in RPMI medium (1), and 2×10$^5$ responder cells were mixed with an equal number of gamma-irradiated (5000 rads) B6 stimulator cells and cultured for 5 days in a 96-well round-bottomed microliter plate. During the last 18 hours of culture, 1 micro-Ci of tritiated thymidine (ICN Radiochemicals, Irvine, Calif.) was added to each well. The incorporation of the radioisotope into newly synthesized DNA was determined by harvesting the cells with an automated sample harvester and by liquid scintillation counting.

Removal of T cells

In certain experiments T lymphocytes and T cell subsets were depleted by the use of monoclonal antibodies and complement as described previously (32).

Effect of indomethacin and cycloheximide on the generation of the suppressive supernatants Pam 212 cells were treated with UV-radiation as described above. Immediately after exposure, 10 micrograms/ml of indomethacin or 10 micrograms/ml of cycloheximide was added to the cultures (Sigma Chemical Co., St. Louis, Mo.). 24 hr later the supernatants were collected and the low molecular weight inhibitors were removed by dialysis against PBS (Spectrophore dialysis tubing, 6–8000 molecular weight cut off, Fisher Scientific, Houston, Tex.). The supernatants were injected i.v. into C3H mice that were sensitized with BALB/c spleen cells as described above. A one way MLR against allogeneic spleen cells was set up 7 days later as described previously.

Lectin affinity columns.

Supernatants from the UV-irradiated or control keratinocytes (100 µg total protein) were added to Con A bound to agarose (0.5 ml packed gel, Sigma Chemical Co.). The supernatants and the Con A-agarose were mixed together at 4° for 30 minutes, and then added to a 1 ml syringe. The unbound material was eluted with 5 ml of PBS. The bound material was eluted by adding 5 ml of 1M-α-methyl-D-glucoside followed by 5 ml of 1M α-methyl-D-mannoside. Both the unbound and bound materials were concentrated by ultrafiltration, and 10µg was injected into C3H mice. Five days later, the animals were sensitized with alloantigen as described above, and the suppression of the MLR was used to indicate which fraction retained the suppressive activity. The fractions from the Con A columns were further analyzed by SDS-PAGE under reducing and non-reducing conditions according to the methods described by Laemmli (42). The proteins were visualized by silver staining (Bio-Rad, Rockville Centre, N.Y.).

IL-1 bioassay.

Il-1 activity was measured by the proliferation of the IL-1 dependent murine helper cell line D10.G4.1.1 as described (25). The cells (10$^4$ per well) were added to a 96-well microliter dish in medium containing 2.5 µg/ml of Con-A (Sigma Chemical Co. St. Louis, Mo.) together with various dilutions of the supernatants from the UV-irradiated or control keratinocytes. In addition, various amounts of murine rIL-1 (Genzyme Corp. Boston, Mass.) was used to generate a standard curve. After a 48 hour culture period, 1µCi/well of tritiated thymidine was added and 24 hours later the cells were harvested on glass fiber filters and the radioactivity incorporated was measured as described above.

Statistical analysis

The two tailed Student's t-test was used to determine statistically significant differences between experimental and control groups. In experiments in which DTH was used as a measure of immune responsiveness, there were 5 mice per group. In experiments in which the MLR response was measured there were generally 2-3 mice per group. The response of each individual animal was measured and the data pooled. Each experiment was repeated at least twice.

RESULTS

Effect of supernatants from UV-irradiated keratinocytes on the immune response to alloantigens. Previous reports from this laboratory demonstrated that exposure of mice to UV radiation prior to immunization suppressed the induction of DTH to alloantigen (31, 32). The injection of supernatants from UV-irradiated keratinocytes was studied to determine if it could mimic the effect of total-body UV irradiation and suppress DTH. Mice were injected with the suppressive supernatants or exposed to 40 kJ/m² of UV radiation. Control mice were shaved but not irradiated or injected with supernatants from non-irradiated Pam 212 cells. Five days later the mice were sensitized with alloantigen. DTH to the alloantigen was then measured 7 days later. The data presented in Table 7 demonstrate that mice injected with supernatants from UV-irradiated epidermal cells exhibit little or no response against allogeneic cells.

TABLE 7

EFFECT OF SUPERNATANTS FRON UV-IRRADIATED KERATINOCYTES ON DTH

| | Treatment[a] | footpad[b] thickness | Specific footpad swelling | %[c] suppression | P>[d] |
|---|---|---|---|---|---|
| Exp. 1 | NONE | 2 ± 3 | 0 | | |
| | NR | 42 ± 7 | 40 | 0 | |
| | UV | 19 ± 11 | 17 | 58 | .001 |
| | Pam SN | 32 ± 9 | 30 | 25 | NS |
| | UV-Pam SN | 19 ± 4 | 17 | 58 | .001 |
| Exp. 2 | NONE | 13 ± 5 | 0 | | |
| | NR | 41 ± 6 | 28 | | |
| | UV | 26 ± 4 | 13 | 54 | 0.001 |
| | UV-L9295N | 33 ± 6 | 20 | 29 | NS |
| | UV-J774.1SN | 35 ± 4 | 22 | 21 | NS |
| Exp. 3 | NONE | 3 ± 3 | 0 | | |
| | NR | 21 ± 3 | 18 | 0 | |
| | UV | 9 ± 5 | 6 | 67 | .001 |
| | Pam SN | 29 ± 6 | 26 | 0 | NS |
| | UV-Pam SN | 4 ± 4 | 1 | 95 | .002 |

[a]Mice were injected i.v. with SN from UV-irradiated Pam 212 cells (UV-SN), SN from non-irradiated control cells (PAM-SN) or exposed to 40 kJ/m² UV radiation. In experiment 1 and 2, C3H mice were sensitized with BALB/c spleen cells. In Experiment 3, BALB/c mice were sensitized with C3H spleen cells. There were 5 mice per group.
[b]Units: cm × 10⁻³;
[c]% suppression = [1 - (specific footpad swelling experimental/specific footpad swelling control)] × 100.
[d]P values determined by two-tailed Student's t-test, experimental vs. NR (non-irradiated control mice,); NS = P > .01.

The response observed in mice previously exposed to UV was significantly less than that observed in the non-irradiated control mice (NR). Similarly, the response seen in mice injected with supernatants from the UV-irradiated Pam 212 cells was significantly suppressed, whereas, the injection of supernatants from the non-irradiated Pam 212 cells did not cause a significant suppression of DTH. It should be noted that the Pam 212 cell line is of BALB/c origin. Because the intravenous introduction of foreign histocompatibility antigens can suppress DTH (37) it is possible that the suppression observed in Experiment 1 was an artifact resulting from the release of H-2 antigens into the supernatant by the UV-irradiated Pam 212 cells. To rule out this possibility, supernatants from UV-irradiated Pam 212 cells were injected into BALB/c mice (Experiment 3, Table 7). These mice were then immunized with C3H spleen cells. The DTH response of BALB/c mice to C3H antigens was also suppressed, suggesting that the effect could not be attributed to the release of alloantigens into the medium by the irradiated Pam 212 cells. These data also indicate that the induction of suppression by the supernatants is not H-2 restricted.

The presence of suppressor cells in the spleens of mice in which the DTH response was depressed was investigated.

As shown in Table 8, transfer of spleen cells from mice injected with supernatants from the UV-irradiated Pam 212 cells (UV Pam 212 SN) could inhibit the induction of DTH in normal recipient animals.

TABLE 8

ANTIGEN-SPECIFIC SUPPRESSOR CELLS ARE PRESENT IN THE SPLEENS OF MICE INJECTED WITH SUPERNATANTS FROM UV-IRRADIATED KERATINOCYTES

| Source of[a] donor cells | Sensitizing antigen suppression | footpad[b] thickness | specific swelling[b] | %[b] |
|---|---|---|---|---|
| none | none | 14 ± 5 | 0 | |
| none | BALB/c | 57 ± 13 | 43 | — |
| Pam 212 SN | BALB/c | 57 ± 13 | 43 | 0 |
| UV Pam 212 SN | BALB/c | 35 ± 5[*c] | 21 | 51 |
| none | none | 17 ± 5 | 0 | |
| none | B6 | 32 ± 7 | 15 | — |
| Pam 212 SN | B6 | 38 ± 8 | 21 | 0 |
| UV Pam 212 SN | B6 | 36 ± 7 | 19 | 0 |

[a]Donor mice were injected with from supernatants (10 micrograms of protein) from the non-irradiated control Pam 212 cells or the UV-irradiated keratinocytes. 5 days later all the donor mice were injected with 5 × 10⁷ BALB/c spleen cells. DTH of the donor mice was read 7 days after sensitization and 1 × 10⁸ donor spleen cells were transferred into two groups of recipient mice. One group was sensitized with BALB/c spleen cells, the second with B6 spleen cells; DTH of the recipient mice against the sensitizing antigen was read 7 days later. The background response was measured in mice that were not sensitized but were challenged with the antigen.
[b]See footnotes for Table 7.
[c]*P < 0.0001 two tailed Student's t-test. vs the control.

The injection of spleen cells from mice injected with control supernatants (Pam 212 SN) did not significantly suppress the recipient animals' immune response. The specificity of the suppression was also examined. Spleen cells from C3H mice, injected with the supernatants from the UV-irradiated keratinocytes and sensitized with BALB/c cells, were transferred into normal C3H mice. The recipients were then sensitized and challenged with B6 spleen cells. While the transfer of suppressor cells from mice injected with the suppressive supernatants and sensitized with BALB/c cells did suppress DTH when the recipients were sensitized with BALB/c cells, these cells had no effect on the magnitude of the DTH response against B6, indicating the specificity of the suppressor cells.

The effect of injecting supernatants from the UV-irradiated keratinocytes on the ability of spleen cells from treated mice to generate a MLR was also examined. C3H mice were injected with supernatant from the UV-irradiated keratinocytes (10 micrograms of protein) or exposed to UV radiation. Five days later all the mice were injected with B6 spleen cells. This was done because a previous study had demonstrated that in order to suppress the MLR, mice must be first exposed to UV radiation and then sensitized with the alloantigen. Exposure to UV radiation alone will not induce suppression [6]. Seven days later, spleen cells from these mice were used as responder cells in the MLR. As shown in Table 9, spleen cells from mice injected with the supernatants from the UV-irradiated keratinocytes do not proliferate in response to the alloantigen.

TABLE 9

INABILITY OF SPLEEN CELLS FROM MICE INJECTED WITH THE SUPERNATANT FROM UV-IRRADIATED KERATINOCYTES TO PROLIFERATE TO ALLOANTIGEN

| | γCPM | | | |
|---|---|---|---|---|
| | Experiment 1 | | Experiment 2 | |
| Treatment | 3 day | 5 day | 3 day | 5 day |
| NR | 62994 ± 4088 | 30633 ± 1312 | 60182 ± 9571 | 42489 ± 5633 |
| UR | 6952 ± 1738* | 7049 ± 736* | 32026 ± 3856* | 13206 ± 4472* |
| Pam 212 SN | 55113 ± 6304 | 43255 ± 4403 | 59490 ± 5894 | 37804 ± 2361 |
| UV Pam 212 SN | 7236 ± 2395* | 6219 ± 1395* | 31056 ± 4915* | 22175 ± 2654* | a. Spleen cells were obtained from the non-irradiated controls (NR), mice exposed to 46 kJ/m² of UV radiation (UV), mice injected with supernatants from the non-irradiated control cultures. (Pam SN), or mice injected with supernatants (10 μg protein) from the UV-irradiated keratinocytes (UV Pam SN). All mice were sensitized with alloantigen 5 days after UV exposure or injection of the keratinocyte-derived supernatants. Cells were cultured with gamma-irradiated allogeneic stimulator cells for 3 or 5 days. Data is expressed as Δ CPM; the background response of the responder cells cultured alone was subtracted.
*$P < 0.001$, two-tailed Student's t-test vs. the NR control.

Compared to the response seen in the control (normal mice immunized with alloantigen, NR), exposure of mice to UV-radiation prior to sensitization, or injecting the supernatant from the UV-irradiated keratinocytes, caused a significant depression of the proliferative response. The injection of the supernatant from the non-irradiated keratinocytes had no suppressive effect ($P>0.05$). Note that the cells were harvested after 3 or 5 days of culture. Regardless of duration of the culture period, exposure of mice to UV radiation or injecting the supernatant from the UV-irradiated keratinocytes, resulted in a significant suppression ($P<0.001$) of the proliferative response. Thus a simple shift in the kinetics of the response does not explain the observed suppression of proliferation. The enhanced response of the 3 day cultures can be explained by the fact that the cells were isolated from mice that were injected with alloantigen. Since however, normal cells do not proliferate to alloantigen after a 3-day culture (data not shown) we have chosen to use the 5 day culture period in all further experiments so that the specificity of the suppression can be measured.

To examine the specificity of the suppression, spleen cells were obtained from mice injected with the suppressive supernatants and sensitized with B6 cells. As before, when these cells were cultured with gamma-irradiated B6 stimulator cells there was little to no proliferation (Table 10).

TABLE 10

SPECIFICITY OF THE SUPPRESSION INDUCED BY INJECTING SUPERNATANTS FROM UV-IRRADIATED KERATINOCYTES

| | Treatment of mice* | CPM ± SEM | | |
|---|---|---|---|---|
| | | cells alone | cells + B6 | cells + BALB/c |
| Exp. 1 | Medium + B6 cells | 3188 ± 667 | 31592 ± 2519 | 33382 ± 1149 |
| | Pam 212 SN + B6 cells | 4250 ± 134 | 30157 ± 1325 | 32065 ± 2330 |
| | UV Pam 212 SN + B6 cells | 4428 ± 687 | 15550 ± 3883* | 35622 ± 283 |
| Exp. 2 | Medium + B6 cells | 862 ± 372 | 53780 ± 9676 | 34416 ± 5700 |
| | Pam 212 SN + B6 cells | 2960 ± 832 | 61428 ± 7100 | 70764 ± 6515 |
| | UV Pam 212 SN + B6 cells | 2749 ± 450 | 25472 ± 4428* | 37448 ± 5724 |

TABLE 10-continued

SPECIFICITY OF THE SUPPRESSION INDUCED BY INJECTING SUPERNATANTS FROM UV-IRRADIATED KERATINOCYTES

| Treatment of mice* | CPM ± SEM | | |
|---|---|---|---|
| | cells alone | cells + B6 | cells + BALB/c |
| Medium + BALB/c cells | 940 ± 388 | 32576 ± 6656 | 57138 ± 8292 |
| Pam 212 SN + BALB/c cells | 3720 ± 2068 | 45196 ± 5330 | 50732 ± 8988 |
| UV Pam 212 SN + BALB/c cells | 2740 ± 576 | 53526 ± 4060 | 20052 ± 3224* |

*Mice were injected with supernatants from the UV-irradiated keratinocytes (UV Pam 212 SN) or supernatants from the control cells (Pam 212 SN) and then sensitized with B6 or BALB/c spleen cells. The proliferative response of their spleen cells was compared to the response of the normal control spleen cells.
*$P < 0.001$ two-tailed Student's T-test.

When the same cells were cultured with BALB/c stimulator cells rather than B6 stimulator cells, they generated a MLR that was indistinguishable from that of the normal control cells (Exp. 2). These findings demonstrate that like the suppression induced by exposure of mice to UV, the suppression induced by injecting supernatants from UV-irradiated Pam 212 cells was specific for the antigen subsequently used to sensitize the animal.

To determine whether T-cells were responsible for suppressing the MLR, spleen cells from C3H mice, injected with the suppressive supernatants and sensitized with B6 were treated with anti-Thy 1.2 monoclonal antibody and complement. The remaining cells were added to cultures of normal C3H spleen cells and gamma-irradiated BALB/c stimulator cells. The data from this experiment shown in FIG. 6, demonstrate that Ts are generated in the spleens of mice injected with supernatants from the UV-irradiated Pam 212 cells. Whereas the addition of complement treated cells (C3H +B6+UV) caused a significant suppression of the MLR ($P<0.001$) compared to the control, C3H +B6), the depletion of T lymphocytes totally abrogated the suppressive effect. In addition, depletion of the Lyt 1+ subset of T cells also also caused a total abrogation of suppression. Depletion of the Lyt 2+ cells had no effect on the suppression of the MLR. Irradiation of the suppressor cells with 20

Gy of gamma radiation reduced the suppressive effect to a degree, however there was still a significant difference from the control (P<0.001). As for the specificity of the suppression, the addition of spleen cells from mice initially injected with the suppressive supernatants and sensitized with B6 cells had no suppressive effect when BALB/c spleen cells were used as stimulators (34528±4868 CPM, C3H+B6) compared with (31983±4524 (PM, C3H+B6 UVB) when supernatants from the UV-irradiated Pam 212 cells were injected). Thus, a Thy 1+Lyt 1+, 2−, radiation resistant, antigen-specific suppressor cell is induced after injecting the supernatants from the UV-irradiated keratinocytes into mice.

Figure 7B:
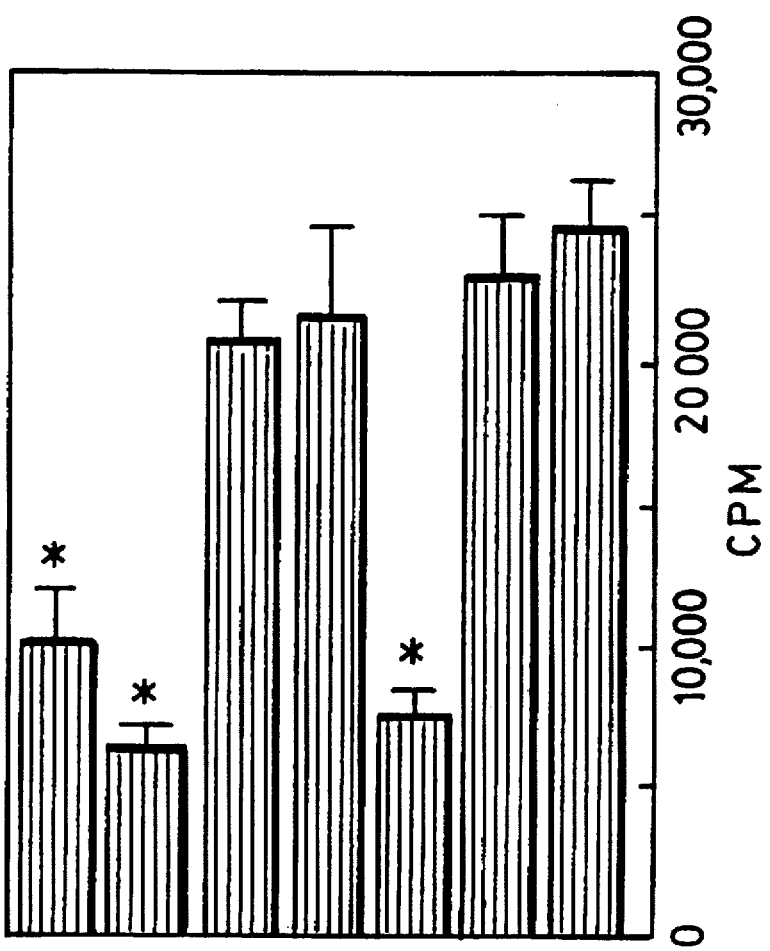

Certain characteristics of the suppressive material are shown in FIG. 7. In this experiment two approaches were used. In panel A, the Pam 212 cells were exposed to UV and then treated with either the prostaglandin synthetase inhibitor, indomethacin or with cycloheximide, which interferes with protein synthesis. Twenty-four hours later all the supernatants were collected, dialyzed to remove the low molecular weight inhibitors and injected into mice. Note that the inhibition of protein synthesis interferes with the ability of the UV-irradiated cells to generate the suppressive cytokine, while the inhibition of prostaglandin synthesis did not. Dialysis had no effect on the ability of the supernatant from the UV-irradiated keratinocytes to suppress the induction of the MLR. In panel B the supernatants from the UV-irradiated keratinocytes were collected and heated, boiled or treated with 10 micrograms/ml of trypsin. Compared to the controls (mice injected with media or supernatants from the non-irradiated cells) injection of the supernatant from the UV-exposed keratinocytes suppressed the generation of the MLR. Boiling the supernatant or treating it with trypsin totally removed the suppressive effect. Exposure to 56° C. for 30 minutes or 1 hr had no effect on the ability of the supernatant to suppress the MLR. The conclusion from these data is that the suppressive cytokine released from UV-irradiated keratinocytes is a non-prostaglandin like, non-dialysable protein.

An intriguing and not completely answered question about the suppression induced by such UV-radiation is; how does exposure of the dorsal skin of mice to UV radiation result in a systemic suppression of the immune response, one that is characterized by the appearance of splenic antigen-specific suppressor T cells? Clearly, the UV radiation is not penetrating to the spleen [33], so direct irradiation of the T cells of the spleen is not possible. While a variety of theories have been proposed, most of the experimental evidence to date support the concept that UV-induced soluble suppressive factors are involved. A review of the literature, however, indicates that the exact role of soluble factors in the induction of suppression by UV radiation is not clear. Swartz [8] found that when plasma from UV-irradiated animals was transferred into normal recipients, their ability to respond to contact allergens was significantly suppressed. Harriott-Smith and Halliday [9] also described the presence of suppressive factors in the serum of UV-irradiated mice. DeFabo and Noonan [10] have suggested that the photoreceptor for UV-radiation in the skin may be urocanic acid. They suggest that the photoisomerization of trans-urocanic acid to cis-urocanic acid by UV is essential in the induction of systemic suppression. Data to support this hypothesis come from the experiments of Ross et al. [3]) and Noonan et al. [12] demonstrating the injection of cis-urocanic acid can suppress DTH to Herpes Simplex Virus and result in an impairment of splenic antigen-presenting cell function. An alternative hypothesis comes from the studies of Robertson et al. [13] where the injection of recombinant interleukin-1 (IL-1) into mice prevented them from responding to contact allergens. Suppressor cells were found in the spleens of these mice that could inhibit the elicitation of CHS when transferred into sensitized animals. The suppression by IL-1 appears to be dependent on the release of prostaglandin since the administration of the prostaglandin synthetase inhibitor, indomethacin abrogated the suppressive effect. These authors suggest that the inflammation caused by UV exposure results in the release of substances such as IL-1 and prostaglandins which play a role in the induction of the systemic suppression. Studies by Gahring et al. [14] demonstrating increased levels of IL-1 in the serum of UV-irradiated mice support this hypothesis. It should be noted, however, that Harriott-Smith and Halliday [9] were unable to document the presence of IL-1 in the serum samples that suppressed CHS in their study. Swartz found his suppressive material had a molecular weight between i to 10 kilodaltons suggesting it is not cis-urocanic acid [38]. Finally, Schwarz et al. [35, 36] showed that UV-treatment of primary epidermal cell cultures and/or a keratinocyte cell line in vitro resulted in the release of suppressive cytokines into the supernatant. Injection of the supernatant into mice could mimic the effect of whole body UV-irradiation and suppress the animals' ability to respond to contact allergens. It is of interest to note that that use of indomethacin in this study did not abrogate the production of the suppressive factor. While these data support a role for soluble suppressive factors in the systemic suppression of the immune response by UV radiation the exact nature of the factor responsible for the systemic suppression of the immune response after UV exposure can not be completely defined from these studies.

Because the limited penetration of UV radiation confines its primary effect mainly to the skin, the release of soluble suppressive factors by UV-treated epidermal cells is an attractive hypothesis to explain the systemic suppression of the immune response by UV radiation. The present invention relates to using specific UV radiation to suppress, in an antigen-specific manner, the immune response to alloantigen. The ability of cytokines from UV-irradiated keratinocytes to induce alloantigen specific suppressor T cells was tested as described herein. These data demonstrate the following: (1) DTH to alloantigens can be suppressed by the factor released from UVB-irradiated keratinocytes; (2) the suppressive activity of the factor is not H-2 restricted; (3) suppressor cells are induced; (4) the suppressor cells are specific for the antigen used to sensitize the mice injected with the suppressive cytokine; and (5) the suppressor cells are T cells. Since the immunosuppression induced by the injection of this factor is very similar to that seen after exposure of mice to UV radiation [6, 32], these findings support the hypothesis that the systemic suppression of DTH in vivo following UVB-irradiation is the result of the release of suppressive cytokines by UVB-irradiated keratinocytes.

The identity of the suppressive substance is not totally defined at the present time. The fact that the activity was not abrogated by indomethacin treatment and that the activity was retained after dialysis suggest that this factor is not prostaglandin or urocanic acid. In addition, HPLC analysis was unable to demonstrate the presence of cis-urocanic acid in the suppressive supernatant. The removal of all suppressive activity by cycloheximide treatment of the cells and/or trypsin treatment of the supernatant strongly suggest the protein nature of the suppressive material. The active material released by the UV-irradiated keratinocytes was bound to Con A-agarose beads, suggesting that it is a glycoprotein. These data suggest that suppressive cytokines released from UV-irradiated keratinocytes play a role in the induction of alloantigen-specific suppressor T cells. Furthermore, these data suggest that the use of factors released from UV-irradiated keratinocytes may provide a novel approach for suppressing the rejection of organ transplants. The fact that exposure to UV radiation (100 mJ/cm$^2$ to 300 mJ/cm$^2$) has been shown to modulate the production of IL-1 by keratinocytes [39, 40] and the fact that i.v. injection of IL-1 has been shown to suppress the elicitation of CHS in vivo [13], makes IL-1 a potential candidate. However, preliminary studies have suggested that the ability of the supernatants from both the UV-irradiated cells and the control non-irradiated cells to support the proliferation of the IL-1 dependent cell line, D10.G4, is equivalent. Because the immune response is not suppressed with the supernatant from the non-irradiated cells IL-1 is apparently not involved. Whether the factor described herein is similar to that described by Schwarz et al. (35, 36) also remains to be seen. Preliminary studies suggest thought that it is not. CHS was not suppressed with the factor released from the UVB-irradiated keratinocytes. Only after UVA treatment of the cells could a factor be generated that could suppress CHS. The UVA-induced factor would suppress CHS but not DTH and the UVB-induced factor would suppress DTH but not CHS. Thus, it appears that two different suppressive cytokines are released from keratinocytes, depending on the wavelength of light used to irradiate the cells.

Dose of supernatants from UV-irradiated keratinocytes required to induce suppression.

Figure 8:
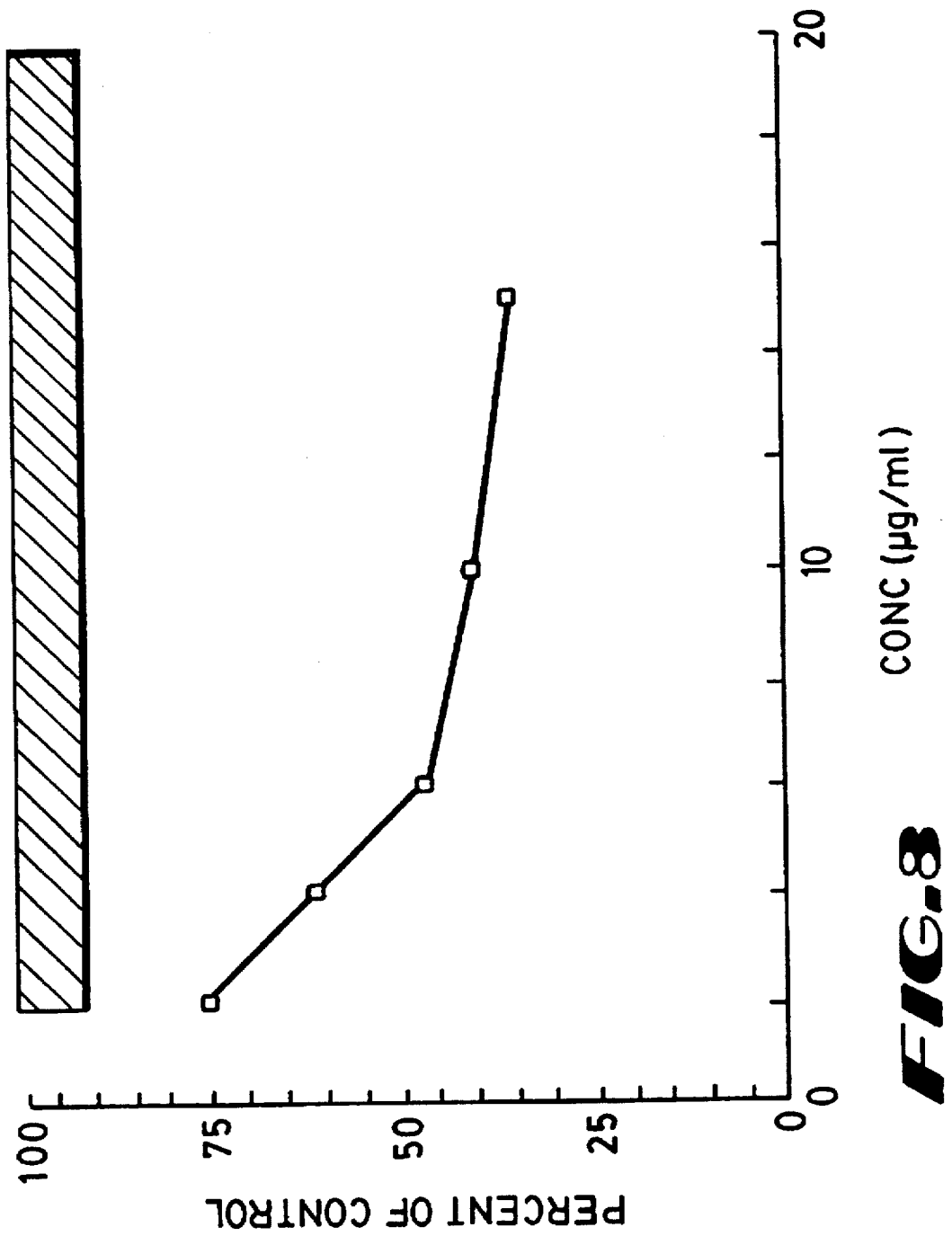
FIG. 8 shows dose-response curve for suppressing the MLR. Various concentrations of culture supernatants from the UV-irradiated keratinocytes were injected into mice and the ability of their spleen cells to proliferate in response to alloantigen was measured. The data are expressed as a percentage of the control response (mice injected with media; 34,456±2215 cpm is equal to 100%; the background response was 3,072±495 cpm). The cross-hatched region represents the proliferation of spleen cells from mice injected with supernatants from non-irradiated keratinocytes.
Figure 9:
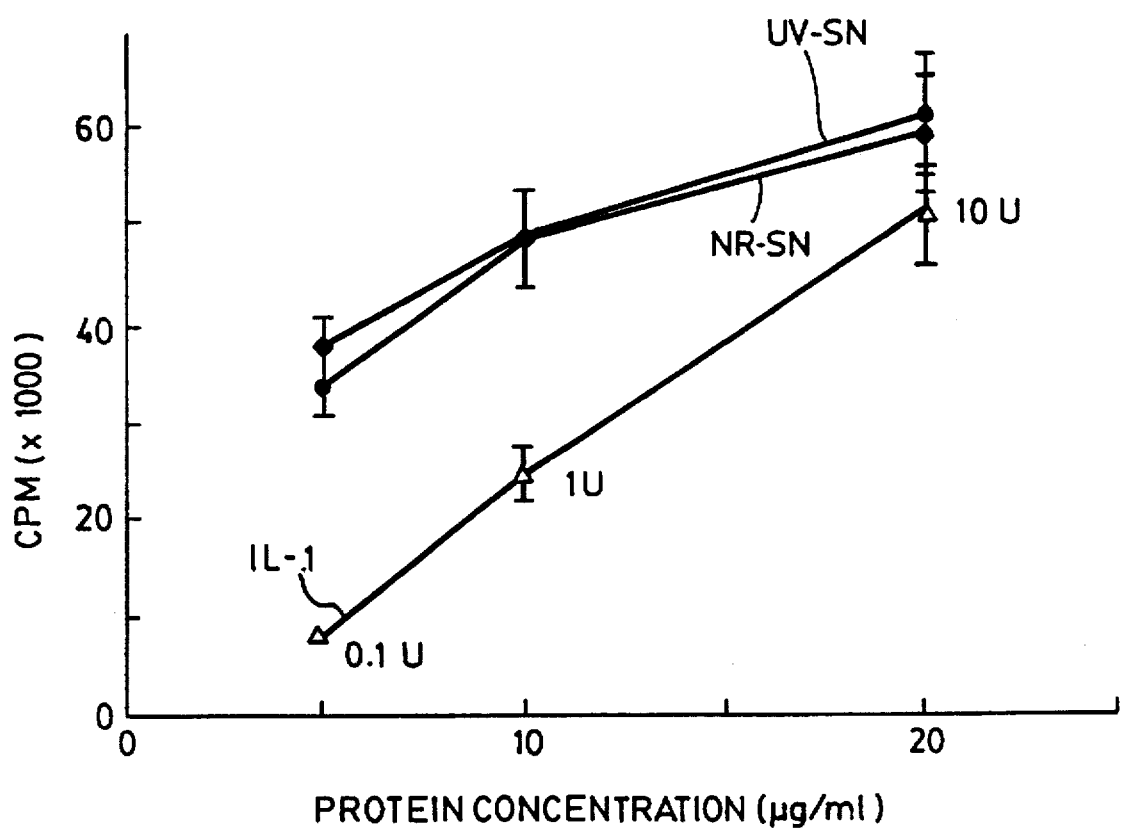
FIG. 9 shows production of IL-1 by the UV-irradiated and control keratinocytes. Supernatants were obtained from the UV-irradiated or control nonirradiated Pam 212 cells. Protein concentration was measured and various concentrations were added to the IL-1 dependent D10.G4.1 helper cell line. A standard curve was generated by adding dilutions of murine rIL-1 to the cells.

The dose-response curve for the suppression of the MLR is shown in FIG. 8. C3H mice were injected with various concentrations of supernatants from the UV-irradiated and non-irradiated keratinocytes and 5 days later were sensitized with B6 cells. One week later their spleens were removed, and the proliferation in response to alloantigen was measured. The control response (34,456 cpm=100%) was determined by measuring the proliferation of spleen cells isolated from mice injected with medium and immunized with alloantigen. Although injecting supernatants from the non-irradiated cells had no suppressive effect, injecting increasing amounts of supernatants from the UV-irradiated keratinocytes increased the degree of suppression. From these data, we determined that the amount of suppressive material needed to cause a 50% suppression of the response was between 7 and 10 µg of protein. Therefore, in all subsequent experiments at least 10 µg of protein was injected.

Measurement of IL-1 present in the supernatants from the UV-irradiated keratinocyte cultures.

Pam 212 constitutively produce IL-1. Because data published by Robertson et al. (20) indicated that iv injection of IL-1 can suppress the induction of a contact hypersensitivity reaction and since UV exposure has been shown to modulate the expression of IL-1 mRNA, and the release of IL-1 by keratinocytes (27, 28) it is possible that the overproduction of IL-1 by our UV-irradiated Pam 212 cells may be responsible for the suppression we see. To address this question we measured the amount of IL-1 released into the medium after exposure of the keratinocytes to UV radiation. The keratinocytes were exposed to UV radiation as described and 18 hours later the supernatants collected and added to the IL-1 dependent, D10.G4.1, T helper cell line. Control supernatants were obtained from keratinocytes treated in an identical manner but not exposed to UV radiation. As can be seen from the data presented in FIG. 8, exposing the Pam 212 cells to 200 J/m$^2$ of UV-radiation did not cause a significant increase in the release of IL-1. The proliferation of the D10.G4. 1 cells cultured with the supernatant from the UV-irradiated Pam 212 cells was identical to that seen when supernatants from the non-irradiated control keratinocytes were used. Because injecting the supernatants from the control non-irradiated keratinocytes cells did not suppress the induction of an immune response, whereas injecting supernatant from the UV-irradiated cells did, we conclude that the release of IL-1 by the keratinocytes is not responsible for the observed suppression.

Binding of the suppressive material to Con A-agarose columns.

Supernatants from the UV-irradiated and control non-irradiated keratinocytes were added to agarose beads coupled with Con A (Table 11).

TABLE 11

Fractionation of the suppressive material on lectin affinity columns

| Fraction injected[a] | CPM ± SEM | | ΔCPM | % Suppression |
|---|---|---|---|---|
| | Cells alone | Cells + BALB/c | | |
| Medium | 5417 ± 294 | 46786 ± 3791 | 41369 | — |
| NR SN | 3394 ± 120 | 39657 ± 4853 | 36263 | 12 |
| UV starting material | 7525 ± 383 | 29833 ± 2537*[b] | 22308 | 47 |
| UV unbound | 5217 ± 525 | 39449 ± 5093 | 34232 | 17 |
| UV glucoside eluate | 5527 ± 850 | 48739 ± 5774 | 43212 | 0 |
| UV mannoside eluate | 5208 ± 1013 | 28815 ± 520*[b] | 23607 | 43 |
| NR unbound | 6232 ± 192 | 46574 ± 7029 | 40342 | 2 |
| NR glucoside eluate | 3122 ± 1643 | 42986 ± 6259 | 39864 | 4 |
| NR mannoside eluate | 4775 ± 981 | 38035 ± 954 | 33260 | 20 |

[a]Supernatants (100 µg of protein) from the control non-irradiated (NR) keratinocytes and the UV-irradiated keratinocytes (UV) were mixed with Con A agarose (0.5 ml packed gel) and incubated at 4° for 30 minutes. The gel was added to 1.0 ml syringes, and 5 ml of PBS was added to elute the unbound material. the bound material was eluted by the addition of 5 ml of 1M α-methyl-D-glucoside followed by 5 ml of 1M α-methyl-D-mannoside. The eluted fractions were dialyzed against PBS, concentrated by ultrafiltration, and 10 µg of protein was injected into C3H mice. The mice were sensitized with alloantigen. The MLR was measured as described in Materials and Methods.
[b]*P < 0.001, Student's two-tailed t-test vs. medium control.

As seen in Table 11, the flow-through material (UV unbound) had little suppressive activity when compared with that of the starting material (UV SN), indicating that the majority of the suppressive material bound to the Con A. Because both α-D-glucosyl and α-D-mannosyl residues bind to Con A, an attempt was made to elute the bound material by competition with excess amounts of α-methyl-D-glucoside and α-methyl-D-mannoside. The suppressive activity was found in the fraction eluted with the mannoside (UV mannoside eluate) but not with the glucoside (UV glucoside eluate). No significant suppression was noted when the control supernatants was fractionated on the Con A-agarose columns (NR mannoside eluate, NR glucoside eluate). The eluted suppressive fractions and the controls were then analyzed by SDS-PAGE under reducing conditions (FIG. 10). The major difference noted between the suppressive material (UV mannoside eluate, lane 1) and the non-suppressive fractions was the appearance of a unique band with a molecular weight of 68 kDa. Because this band was present only in the fraction that induced suppression (UV mannoside eluate), and was absent from all the other fractions that did not have any suppressive activity [UV glucoside eluate (lane 2), NR mannoside eluate (lane 3) and NR glucoside eluate (lane 4)], these data suggest that the molecular weight of the suppressive material is 68 kda. An identical migration pattern was observed when the material was electrophoresed under non-reducing conditions.

Because the ability of the supernatants from both the UV-irradiated cells and the control non-irradiated cells to support the proliferation of the IL-1-dependent cell line, D10.G4.1 is equivalent it does not appear that the overproduction of IL-1 by the UV-irradiated keratinocytes is responsible for the suppression we describe. The suppressive factor described here binds to concanavalin-A agarose columns, indicating that it is a glycoprotein, whereas IL-1 is not glycosylated, further indicating that the suppression of DTH observed after injecting the supernatants from the UV-irradiated keratinocytes was not due to the injection of IL-1.

SDS-PAGE analysis indicates the presence of a unique 68 kDa band in the fractions that suppressed the induction of the MLR (UV mannoside eluate material) but not in the non-suppressive fractions (UV glucoside eluate, NR glucoside eluate, and NR mannoside eluate). These data indicate that the 68 kDa protein causes the present immunosuppression. Further purification of the suppressive material and testing of the activity of the 68 kDa protein will be carried out to more completely define this protein. Other cells capable of producing such an immunosuppressive glycoprotein such as keratinocytes or other epidermal cells, it is believed, may also be used as a source of the 68 kDa glycoprotein. Likewise, this immunosuppressive glycoprotein should prove useable to preclude undesired immune responses as described elsewhere herein for crude cellular UV-induced cell products.

There are several similarities between the immunosuppression induced by UV radiation and that induced by thermal injury. The presence of I-J+Lyt 1+2− Ts cells in the spleens of mice early after thermal trauma [41] and the presence of similar cells in the spleens of mice following UV irradiation and antigenic sensitization [32] may lead to speculation that a similar mechanism is involved in their induction. Perhaps the release of soluble products from damaged epidermal cells is involved in the induction of suppressor cells in both these systems.

A major goal of transplantation biology is to suppress, in an antigen-specific manner, the response of the host against a foreign graft. Perhaps the most Significant aspect about the data presented herein is the ability to use supernatants from UV-irradiated keratinocytes or analogous preparations with the 68 kDa glycoprotein to suppress, in an antigen-specific manner, the immune response to alloantigen. It may be possible therefore to use this factor to induce antigen-specific suppressor cells and suppress the rejection of foreign tissue grafts. Thus, the injection of suppressive cytokines from UV-irradiated keratinocytes should provide a novel method of inducing a specific suppression of allograft rejection.

The following literature references are incorporated in pertinent part by reference herein for the reasons cited in the text.

REFERENCES

1. Kripke: Immunologic unresponsiveness induced by UV radiation. Immunol. Rev. 80: 102-87, 1984.

2. Kripke et al.: In vivo immune responses during carcinogenesis. JNCI 59:1227–1230, 1977

3. Noonan et al.: Suppression of contact hypersensitivity by UV radiation: An experimental model. Springer Semin. Immunopath. 4:293–2304, 1981

4. Greene et al.: Impairment of antigen-presenting cell function by UV radiation. Proc. Natl. Aca. Sci USA 76:6591–6595, 1979

5. Ullrich S E, Azizi E, Kripke M L: Suppression of the induction of DTH reactions in mice by a single exposure to UV radiation. Photochem. Photobiol. 43:633–638, 1986

6. Ullrich S E: Suppression of the immune response to allogeneic histocompatibility antigens by a single exposure to UV radiation. Transplantation 42:287–291, 1986

7. Molendijk A, van Gurp R J H M, Donselaar I G. Benner R: Suppression of delayed-type hypersensitivity to histocompatibility antigens by ultraviolet radiation. Immunology. 62:299–305, 1987

8. Swartz R P: Role of UVB-induced serum factors in suppression of contact hypersensitivity in mice. J Invest. Dermatol. 83:305–307, 1984

9. Harriott-Smith T G, Halliday W J: Circulating suppressor factors in mice subjected to ultraviolet irradiation and contact hypersensitivity. Immunology 57:207–211, 1986.

10. DeFabo E C, Noonan F P: Mechanism of immune suppression by ultraviolet irradiation in vivo. I. Evidence for the existence of a unique photoreceptor in skin and its role in photoimmunology. J. Exp. Med. 157:84–98, 1983.

11. Ross J A, Howie S E M, Norval M. Maingay J. Simpson T J: Ultraviolet-irradiated Urocanic acid suppresses delayed hypersensitivity to Herpes Simplex virus in mice. J. Invest. Dermatol. 87:630–633, 1986

12. Noonan F P, DeFabo E C, Morrison H: Cis-Urocanic acid, a product formed by ultraviolet B irradiation of the skin, initiates an antigen presentation defect in splenic cells in vivo. J. Invest. Dermatol. 90:92–99, 1988.

12. Robertson B, Gahring L. Newton, R. Daynes R A: In vivo administration of IL-1 to normal mice decreases their capacity to elicit contact hypersensitivity responses: Prostaglandins are involved in this modification for the immune response. J. Invest. Dermatol. 88:380–387, 1987.

14. Gahring L C, Baltz M B, Pepys M. Daynes R A: The Effect of UV Radiation On The Production of ETAF:IL-1 in vivo and in vitro. Proc. Natl. Acad. Sci. USA 81:1198–1202, 1984.

15. Schwarz T., Urbanska A., Gschnait F. Luger T A: Inhibition of the induction of contact hypersensitivity by a UV-mediated epidermal cytokine. J. Invest. Dermatol. 87:289–291, 1986

16. Fisher M S, Kripke M L: Suppressor T lymphocytes control the development of primary skin cancers in ultraviolet-irradiated mice. Science 216:1133–1134, 1982

17. Lau H, Reemtsma K, Hardy M A. Pancreatic islet allograft prolongation by donor-specific blood transfusions treated with UV irradiation. Science 1983; 221:754.

18. Lsu H, Reemtsma K, Hardy M A. Prolongation rat islet allograft survival by direct UV irradiation of the graft. Science 1984; 223:607.

19. Yuspa S H, Hawley-Nelson, P. Koehler, B. Stanley J R: A survey of transformation markers in differentiating epidermal cell lines. Cancer Research 40:4694–4703. 1980.

20. Shearer G M: Cell-mediated cytotoxicity to trinitrophenyl-modified syngeneic lymphocytes. Eur. U. Immunol. 4:527–533. 1974

21. Mishell R I, Dutton R W: Immunization of dissociated spleen cell cultures from normal mice. J. Exp. Med. 126, 423–442, 1967.

22. Jerne N K, Nordin A A: Plaque formation in agar by single antibody producing cells. Science. 140:405–406, 1963.

23. Dunnett C: A multiple comparison procedure for comparing several treatments with a control. J. Am. Star. Assoc. 50:1096–1124, 1955

24. Storb R. Critical issues in bone marrow transplantation. Transplant Proc 1987; 19:2772.

25. Klein J, Chiang C-L, Lofgreen J, Steinmullef D. Participation of H-2 regions in heart transplant rejection. Transplantation 1986; 22:384.

26. Korngold, R, Sprent J. Surface markers of T cells causing lethal graft versus host disease to class I vs. class II H-2 differences. J Immunol. 1985; 135:3004.

27. Fidler, I J. The relationship of embolic homogeneity, number, size and viability to the incidence of experimental metastases. Eur J Cancer 1973; 9:223.

28. Kripke M L. Latency, histology, and antigenicity of tumors induced by UV light in three inbred mouse strains. Cancer Res 1977; 37:1395.

29. Ullrich S E, Kripke M L. Mechanisms in the suppression of tumor rejection produced in mice by repeated UV irradiation. J Immunol 1984; 133:2786.

30. Ullrich S E, Yee G K, Kripke M L. Suppressor lymphocytes induced by epicutaneous sensitization of UV-irradiated mice control multiple immunological pathways. Immunology 1986; 58:185.

31. Ullrich S E. Suppression of the immune response to allogeneic histocompatibility antigens by a single exposure to UV radiation. Transplantation 1986; 42: 287.

32. Ullrich, S. E. and M. Magee. 1988. Specific suppression of allograft rejection after treatment of recipient mice with UV-radiation and allogeneic spleen cells. Transplantation 46:115.

33. Evertt, M. A., Yeargers, E., Sayre, R. M., and R. L. Olson. 1966. Penetration of epidermis by ultraviolet rays. Photochem. Photobiol. 5:533.

34. Ross, J. A., Howie S. E. M., Norval, M., and J. Maingay. 1988. Systemic administration of urocanic acid generates suppression of the delayed type hypersensitivity response to Herpes Simplex Virus in a murine model of infection. Photodermatology 5:9.

35. Schwarz, T., Urbanska, A., Gschnait, F., and T. A. Luger. 1986. Inhibition of the induction of contact hypersensitivity by a UV-mediated epidermal cytokine. J. Invest. Dermatol. 87:289.

36. Schwarz, T., Urbanska, A., Gschnait, F., and T. A. Luger. 1987. UV-Irradiated epidermal cells produce a specific inhibitor of IL-1 activity. J. Immunol. 30 138:1457.

37. Liew, F. Y. 1982. Regulation of delayed type hypersensitivity. VI Antigen-specific suppressor T cells and suppressor factor for DTH to histocompatibility antigens. Transplantation 33:69.

38. Swartz, R. P. 1986. Suppression of DTH to UV radiation induced tumor cells with serum from UVB-irradiated mice. JNCI 76:1181.

39. Kupper, T. S., Chua, A. O., Flood, P., McGuire, J., and U. Gubler. 1987. Interleukin i gene expression in cultured human keratinocytes is augmented by ultraviolet irradiation. J. Clin. Invest. 80:430.

40. Ansel, J. C., Luger, T. A., Lowy, D., Perry, P., Roop, D. R., and J. D. Mountz. 1988. The expression and modulation of IL-la in murine keratinocytes. J. Immunol 140:2274.

41. Kupper, T., and D. R. Green. 1984. Immunoregulation after thermal injury: sequential appearance of I-J$^+$, Lyt 1 T suppressor inducer cells and Lyt 2 T suppressor effector cells following thermal trauma in mice. J. Immunol. 135:3047.

42. Laemmli, U. K. 1970. Cleavage of structural proteins during the assembly of the head of the bacteriophage T4. Nature 27:680.

I claim:

1. A glycoprotein proteins having the following properties:

(a) binding affinity for concanavalin A-agarose;

(b) a reduced binding affinity for concanavalin A-agarose in the presence of α-D-mannopyranoside;

(c) a suppressive effect on delayed-type hypersensitivity without having an inhibitory effect on mammalian antibody production; and (d) isolatable from a culture of PAM 212 epidermal cells subjected to UVB-irradiation.

2. A glycoprotein preparation obtained by a process having the steps of:

(a) irradiating a plurality of PAM 212 mammalian epidermal cells with UVB-irradiation in an amount of about 10 J/m$^2$ to about 100 kJ/m$^2$;

(b) incubating said cells in a nutrient medium;

(c) separating cells from said nutrient medium;

(d) contacting said nutrient medium with a concanavalin A-agarose affinity matrix; and (e) eluting said glycoprotein preparation from said matrix with α-D-mannopyranoside wherein said glycoprotein preparation has a suppressive effect on delayed-type hypersensitivity without having an inhibitory effect on mammalian antibody production.

* * * * *

UNITED STATES PATENT AND TRADEMARK OFFICE
CERTIFICATE OF CORRECTION

PATENT NO. : 5,696,081

DATED : December 9, 1997

INVENTOR(S) : STEPHEN E. ULLRICH

It is certified that error appears in the above-identified patent and that said Letters Patent is hereby corrected as shown below:

In claim 1, column 34, line 22, delete "proteins" and insert therefor --preparation--.

Signed and Sealed this

Twenty-fourth Day of February, 1998

Attest:

BRUCE LEHMAN

*Attesting Officer*   *Commissioner of Patents and Trademarks*